US012564570B2

(12) United States Patent
Bernhard et al.

(10) Patent No.: US 12,564,570 B2
(45) Date of Patent: Mar. 3, 2026

(54) USE OF LEOLIGIN IN THE PREVENTION OF TISSUE DAMAGE

(71) Applicant: UNIVERSITÄT LINZ, Linz (AT)

(72) Inventors: David Bernhard, Linz (AT); Marina Müller, Gallneukirchen (AT)

(73) Assignee: UNIVERSITÄT LINZ, Linz (AT)

( * ) Notice: Subject to any disclaimer, the term of this patent is extended or adjusted under 35 U.S.C. 154(b) by 409 days.

(21) Appl. No.: 18/024,039

(22) PCT Filed: Aug. 27, 2021

(86) PCT No.: PCT/EP2021/073709

§ 371 (c)(1),
(2) Date: Feb. 28, 2023

(87) PCT Pub. No.: WO2022/043481

PCT Pub. Date: Mar. 3, 2022

(65) Prior Publication Data

US 2023/0310363 A1 Oct. 5, 2023

(30) Foreign Application Priority Data

Aug. 28, 2020 (EP) .................................... 20193276

(51) Int. Cl.
*A61K 31/341* (2006.01)
*A61K 9/00* (2006.01)

(52) U.S. Cl.
CPC ............ *A61K 31/341* (2013.01); *A61K 9/007* (2013.01)

(58) Field of Classification Search
CPC .............................. A61K 31/341; A61K 9/007
See application file for complete search history.

(56) References Cited

U.S. PATENT DOCUMENTS

| | | | |
|---|---|---|---|
| 2004/0019073 | A1 | 1/2004 | Drechsel et al. |
| 2013/0053438 | A1 | 2/2013 | Bernhard et al. |
| 2014/0371306 | A1 | 12/2014 | Stuppner et al. |
| 2017/0157301 | A1 | 6/2017 | Mihovilovic et al. |

FOREIGN PATENT DOCUMENTS

| | | | |
|---|---|---|---|
| DE | 1792207 | A1 | 11/1971 |
| WO | 9712687 | A1 | 4/1997 |
| WO | 9916530 | A1 | 4/1999 |
| WO | 2011009161 | A1 | 1/2011 |
| WO | 2011089161 | A1 | 7/2011 |

OTHER PUBLICATIONS

Danzl et al., "Early inhibition of endothelial retinoid uptake upon myocardial infarction restores cardiac function and prevents cell, tissue, and animal death", Journal of Molecular and Cellular Cardiology, 2019, vol. 126, pp. 105-117.

(Continued)

*Primary Examiner* — Trevor Love

(74) *Attorney, Agent, or Firm* — LOZA & LOZA, LLP; Michael Fedrick

(57) ABSTRACT

The present invention provides for leoligin or a derivative thereof for use in the prevention and/or reduction of tissue damages, wherein leoligin or the derivative thereof is administered systemically to the subject in need thereof.

9 Claims, 15 Drawing Sheets

A

Leoligin

B

5-Methoxyleoligin

(56) References Cited

OTHER PUBLICATIONS

Guntner et al., "HPLC-MS/MS Shows That the Cellular Uptake of All-Trans-Retinoic Acid under Hypoxia is Downregulated by the Novel Active Agent 5-Methoxyleogigin", Jul. 30, 2020, vol. 9, pp. 2048, 13 pages.
Ibrahim et al., "Inhalation drug delivery devices: technology update", Medical Devices: Evidence and Research, Feb. 12, 2015, vol. 8, pp. 131-139.
Hu et al., "Synthesis and Biological Evaluation of a Natural Ester Sintenin and Its Synthetic Analogues", J. Nat. Prod., 2005, vol. 68, No. 3, pp. 342-348.
Linder et al., "Leoligin-inspired synthetic lignans with seclectivity for cell-type and bioactivity relevant for cardiovascular disease", Chemical Science, Jan. 25, 2019, vol. 10, No. 22, pp. 5815-5820.
Messner et al., "5-Methoxyleoligin, a Lignan from Edelweiss, Stimulates CYP26B1-Dependent Angiogenesis in Vitro and Induces Arteriogenesis in Infarcted Rat Hearts in Vivo", PLOS ONE, Mar. 12, 2013, vol. 8, No. 3, e58342.
Richardson et al., "Efficiency in Drug Discovery: Liver S9 Fraction Assay as a Screen for Metabolic Stability", Drug Metabolism Letters, 2016, vol. 10, No. 2, pp. 83-90.
Schwaiger et al., "New Constituents of Leontopodium alpinum and their in vitro Leukotriene Biosynthesis Inhibitory Activity", Planta Med, 2004, vol. 70, No. 10, pp. 978-985.
Extended European Search Report for European Application No. 20193276.1, dated Feb. 18, 2021, 8 pages.
International Preliminary Report on Patentability for International Application No. PCT/EP2021/073709, dated Feb. 28, 2023, 7 pages.
International Search Report for International Application No. PCT/EP2021/073709, dated Dec. 13, 2021, 5 pages.
Written Opinion of the International Searching Authority for International Application No. PCT/EP2021/073709, dated Dec. 13, 2021, 6 pages.
International Search Report for corresponding International Patent Application No. PCT/EP2021/073709, dated Dec. 13, 2021.

A

Leoligin

B

5-Methoxyleoligin

D1-1

D2

D2-2

D3

D4

D5

D6

D7

D8

D9

D10

D11

D13

D14

D15

D16

D17

D18

D19

D20

D21

D22

D23

D24

D25

D26

D27

D28

D29

D30

D31

D32

D33

D34

D35

USE OF LEOLIGIN IN THE PREVENTION OF TISSUE DAMAGE

CROSS-REFERENCE TO RELATED APPLICATIONS

This application is the U.S. national stage of International Patent Application No. PCT/EP2021/073709, filed on Aug. 27, 2021 and entitled USE OF LEOLIGIN IN THE PREVENTION OF TISSUE DAMAGE, which claims the benefit of priority under 35 U.S.C. § 119 from European Patent Application No. 20193276.1 filed on Aug. 28, 2020. The disclosures of the foregoing applications are incorporated herein by reference in their entirety.

Field of the Invention

The present invention generally relates to the use of leoligin and derivatives thereof in the prevention, reduction and/or treatment of tissue damage caused by oxygen deprivation. The invention specifically relates to systemic administration of leoligin and derivatives thereof to prevent, reduce and/or treat hypoxia-induced tissue damage.

Background Art

Due to a variety of events, e.g., vascular occlusion, organic tissue may be undersupplied with oxygen (hypoxia) and nutrients, which leads to irreparable tissue damage (e.g. infarcts, heart attacks, strokes). Various strategies exist to keep this damage as low as possible, but these are usually limited to physical methods (cooling in case of stroke, oxygenation in case of a heart attack).

Currently available pharmacological interventions to minimize these damages are limited to the treatment of secondary effects (administration of nitroglycerin, acetylsalicylic acid, lipid reducers, blood pressure reduction, etc.) and do not provide a direct protective effect on the undersupplied tissue per se. Therefore, immediate admission of the patient to an emergency care facility followed by revascularization procedures which have to be performed as quickly as possible (invasive procedures: catheter-based, surgical) is inevitable.

Myocardial infarction (MI) remains a major cause for morbidity and mortality worldwide and is responsible for about one third of all cases of heart failure. The goal of recent treatment strategies in MI therapy is the induction of “reverse modeling”, meaning the improvement of ventricular function, e.g., by increasing the ejection fraction and the stimulation of angiogenesis and arteriogenesis. Since physiological angiogenesis is slow, one strategy is to induce collateral artery growth to bypass occluded arteries and subsequently reinstate blood supply to the ischemic areas. In this case however, the damage to the heart tissue has already been done.

One strategy to improve blood supply to the tissue is to inject growth factors and cytokines (mainly as gene therapies) directly into the tissue. Unfortunately, many of the experimentally successful treatments failed to show a beneficial effect in clinics.

Injection of 5-methoxyleoligin, a derivative of the lignan leoligin, into the peri-infarction zone has been reported as another potential strategy of pro-angiogenic treatment. Upon direct injection into the peri-infarction zone, 5-methoxyleoligin induced arteriogenesis in vivo in a myocardial infarction rat model (see US2013/0053438A1 and Messner et al. 2013, 5-*Methoxyleoligin, a Lignan from Edelweiss, Stimulates CYP26B1-Dependent Angiogenesis in vitro and Induces Arteriogenesis in Infarcted Rat Hearts in vivo*, PLOS ONE, 8(3):e58342).

Danzl et al. describe that all-trans retinoic acid (ATRA)-mediated signalling aggravates the myocardial infarction (MI) phenotype (Danzl et al. 2019, *Early inhibition of endothelial retinoid uptake upon myocardial infarction restores cardiac function and prevents cell, tissue and animal death*, Journal of Molecular and Cellular Cardiology, 126:105-117). They showed that 5-methoxyleoligin is capable of inhibiting ATRA-signalling and that after induction of MI, in mice, in vivo injection of 5-ML directly into the infarction zone (10 injections per heart) reduces the infarction area.

Lignans can be isolated from Edelweiss roots. WO2011/089161A1, for example, describes compositions for treatment or prevention of angiogenic disorders, wherein the compositions comprise lignan compounds which may be obtained from *Leontopodium alpinum* Cass (Edelweiss).

Edelweiss root extracts show a complex pattern of secondary plant metabolites, of several compound classes like coumarins, lignans, sesquiterpenes, polyacetylenes, diterpenes, and others; see Schwaiger, *Planta Med,* 70(10),978-85 (2004). In general, lignans are polyphenolic plant metabolites derived from phenylalanine, which are synthesized by the coupling of two phenylpropanoid units by a bond between the ß-positions in the propane side chains. One of these lignans which has been isolated from the roots of Edelweiss is leoligin (IUPAC name [(2S,3R,4R)-4-(3,4-dimethoxybenzyl)-2-(3,4-dimethoxyphenyl)tetrahydrofuran-3-yl]methyl (2Z)-2-methylbut-2-enoat].

Even though injection of certain compounds into the tissue may improve blood flow after e.g. an MI event, damage due to hypoxia has already been done to the tissue. Furthermore, direct injection into the tissue, e.g. of the heart, is an invasive procedure that usually cannot be applied in the field or even by patients themselves. Thus, valuable time is lost.

In recent years, drug administration via the lungs has gained importance. It is non-invasive and, in the lungs, administered substances are approximately 90% less metabolized when compared to gastric uptake and metabolism via liver. Furthermore, the lung provides a big surface area (>100 $m^2$) for drug uptake into the blood.

However, many different factors have to be considered to establish a mode of administration involving the respiratory tract and sprays are not always the most efficient way to deliver sufficient amounts of drug. Thus, other routes of administration might also be beneficial.

The respiratory system consists of more than 40 different cells and is mainly made up of the conducting airways and the respiratory region (alveolar region). The conducting airways consist of nasal cavity, sinuses, nasopharynx, oropharynx, larynx, trachea, bronchi and bronchioles, which provide a high filter capacity (removes up to 90% of particles), but have a small surface area and lower regional blood flow.

Therefore, there is an unmet need in the field for means and methods to prevent systemic tissue damage caused by a lack of oxygen supply to tissues and organs.

SUMMARY OF INVENTION

It is the objective of the present invention to provide means and methods for the medical interference in diseases and disorders associated with hypoxia and/or to provide compounds and compositions which prevent tissue damage in a hypoxic event. It is further a specific objective of the present invention to provide means and methods for efficient and easy-to-handle administration of such compounds and compositions, e.g. by the patient at home.

The objective is solved by the subject matter of the present invention.

According to the invention, leoligin or a derivative thereof is provided for use in the prevention and/or reduction of tissue damages, wherein leoligin or the derivative thereof is administered systemically to the subject in need thereof.

According to a specific example, systemic administration is achieved via use of an inhaler, such as e.g. jet-stream inhaler, pressurized metered dose inhaler or dry powder inhaler, or via use of a nebulizer, e.g. a jet nebulizer.

Specifically, leoligin or a derivative thereof, such as 5-methoxyleoligin, is provided as an inhalation spray drug for systemic administration to prevent tissue damage as further described herein.

According to a further specific example, systemic administration is achieved by sublingual and/or buccal administration, e.g. by providing leoligin or the derivative thereof formulated in the form of a tablet, lozenge or solution.

Specifically, said tissue damage is caused by vascular obliteration or is associated with hypoxia.

Specifically, the tissue damage is associated with a disease or disorder selected from the group consisting of coronary artery disease, myocardial infarction, stroke, peripheral arterial disease, peripheral vascular disease, and surgery involving temporary disruption of blood flow.

Specifically, the tissue at risk of damages is selected from the group consisting of heart, brain, kidney, bowel, liver, skeletal muscle, and skin.

Specifically provided herein is a novel method for the prevention and/or reduction of tissue damage associated with hypoxia, wherein a pharmaceutical composition or formulation is administered systemically, preferably via the pulmonary route, to a subject in need thereof.

Specifically provided herein is a formulation or composition comprising leoligin or a derivative thereof, for use in the treatment of a subject at risk of or suffering from tissue damage. Specifically, the subject is at risk of or suffering from coronary artery disease, myocardial infarction, stroke, peripheral arterial disease, or peripheral vascular disease.

According to a specific embodiment, the subject in need of leoligin administration has one or more clinical indicators of coronary artery disease selected from the group consisting of frequency and intensity of anginal symptoms, myocardial perfusion, electrocardiogram tracings, scores on quantitative angina scales, and angiography.

Specifically, the subject in need of administration of leoligin or a derivative thereof is a human subject.

According to a further specific embodiment, leoligin or the derivative thereof is administered by inhalation routes. Specifically, leoligin or the derivative thereof is administered by an inhaler.

According to a further specific embodiment, leoligin or the derivative thereof is administered via the sublingual and/or buccal administration route.

Specifically provided herein is a pharmaceutically acceptable composition of leoligin or a derivative thereof for sublingual or buccal delivery.

Specifically provided herein is a pharmaceutically acceptable composition of leoligin or a derivative thereof for administration via inhalation.

According to a specific embodiment, leoligin or the derivative thereof is administered by non-invasive self-administration.

Specifically provided herein is a method of treating, reducing the severity of, reducing the incidence of, delaying the onset of, or reducing pathogenesis of a disease or disorder associated with tissue damage due to hypoxia, wherein the disease or disorder is preferably selected from the group consisting of coronary artery disease, myocardial infarction, stroke, peripheral arterial disease, peripheral vascular disease, and surgery involving temporary disruption of blood flow.

Specifically, said method of treating comprises administering to a subject in need thereof a pharmaceutically acceptable composition of leoligin or a derivative thereof. Specifically, said pharmaceutically acceptable composition of leoligin or derivatives thereof is administered via the airways, e.g. using an inhaler, or is administered via the sublingual and/or buccal administration route, e.g. by using a pharmaceutically acceptable composition of leoligin or derivatives thereof formulated as tablet, lozenge, powder or liquid solution.

Specifically, leoligin or the derivative thereof is administered in an amount of about 0.15 to 15 mg/kg body weight. Specifically, it is administered at an amount of about 0.2, 0.3, 0.4, 0.5, 0.6, 0.7, 0.8, 0.9, 1.0, 1.1, 1.2, 1.3, or 1.4 mg/kg body weight.

According to a specific embodiment, leoligin or the derivative thereof is administered when in acute need. Acute need may for example be in the event of a stroke or an acute myocardial infarction. Acute need may be due to any situation where tissue is at risk of damage due to vascular obliteration or hypoxia.

According to a further specific embodiment, leoligin or a derivative thereof is administered before and/or after revascularization. Revascularization is typically achieved using lysis therapy, catheters, coronary artery bypass graft (CABG) and the like. Specifically, leoligin or the derivative thereof is administered at least 1 time daily to a patient in need thereof. Specifically, a single dose is administered 1, or 2, or more times daily. Specifically, it is administered for at least 1 week, preferably 2 weeks after revascularization.

According to a specific embodiment, the derivative of leoligin is 5-methoxyleoligin, 5,5-dimethoxyleoligin, or any of the derivatives listed in FIG. 2. Specifically, the derivative comprises the structure D1-1, D2, D2-2, D3, D4, D5, D6, D7, D8, D9, D10, D11, D12, D13, D14, D15, D16, D17, D18, D19, D20, D21, D22, D23, D24, D25, D26, D27, D28, D29, D30, D31, D32, D33, D34 or D35 shown in FIG. 2. According to a preferred embodiment, the derivative of leoligin administered systemically to the subject in need thereof as described herein is 5-methoxyleoligin and/or any one or more of the structures D20, D32, D17, D29, D34, D13, D31, D22, D14, D21, D30, D33, D18 or D15 shown in FIG. 2.

According to a specific embodiment, leoligin or the derivative thereof is provided in a liquid formulation.

According to a further specific embodiment, leoligin or the derivative thereof is provided in a solid formulation.

BRIEF DESCRIPTION OF DRAWINGS

In FIG. 3 the effects of liver S9 extract on 5-ML concentrations over time are depicted. Dots represent median values of three independent experiments. Error bars indicate standard deviations. On the y-axis 5-ML concentration are indicated in μg/L. The x-axis shows the time in minutes and gives the timepoints of measurement 5-ML concentrations. $R^2$ of the first order kinetic exponential function (black line) gave a value of 0,9876. From the elimination constant k the elimination half live was calculated.

FIG. 4 5-ML is eliminated by lung microsomes over time. FIG. 4 shows the changes in 5-ML concentration by lung microsomes over time. Dots represent median values of three independent experiments. Error bars indicate standard deviations. On the y-axis 5-ML concentration are given in μg/L. The x-axis shows the time in minutes and gives the timepoints of measurement of 5-ML concentrations. R2of the first order kinetic exponential function (black line) gave a value of 0,6274. From the elimination constant k the elimination half live was calculated.

FIG. 5 Effects of human saliva on 5-ML concentrations. FIG. 5 shows the changes in 5-ML concentration by pooled human saliva over time. The metabolic stability of 5-ML was determined by 1) adding co-factor solution to the assay and 2) in the absence of co-factor solution in the saliva. Dots indicate median values of three independent experiments. Error bars show standard deviations. The y-axis gives 5-ML concentration in μg/L. The x-axis shows the time in minutes and indicates timepoints when the concentration of 5-ML was measured. $R^2$ of the first order kinetic exponential function (black dotted lines) gives a value of 0,8631 for saliva with co-factor and $R^2$ was 0,9219 for samples without co-factor solution. Using the elimination constant k the elimination half live was calculated.

DESCRIPTION OF EMBODIMENTS

Figure 1:
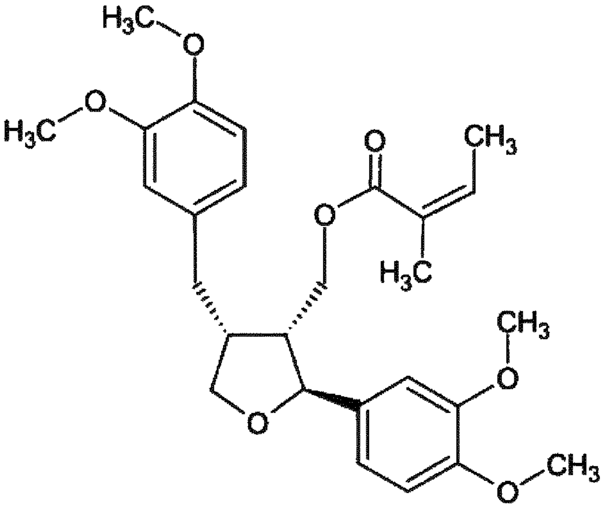
FIG. 1 Structural formula of Leoligin and its derivative 5-methoxyleoligin.
Figure 1:
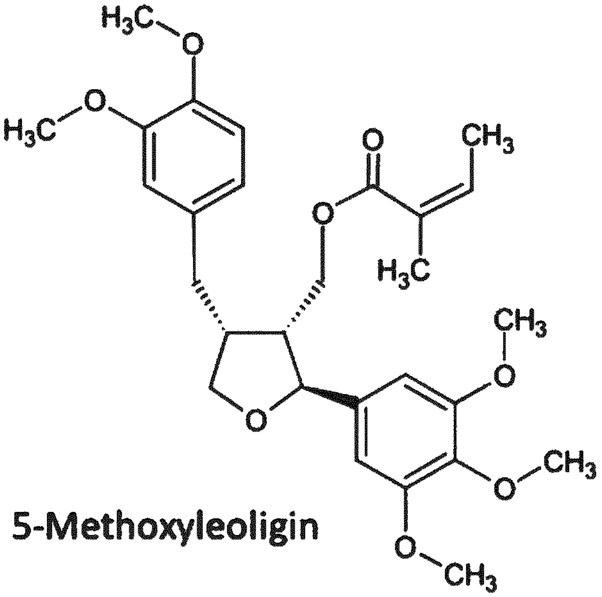
Figure 2:
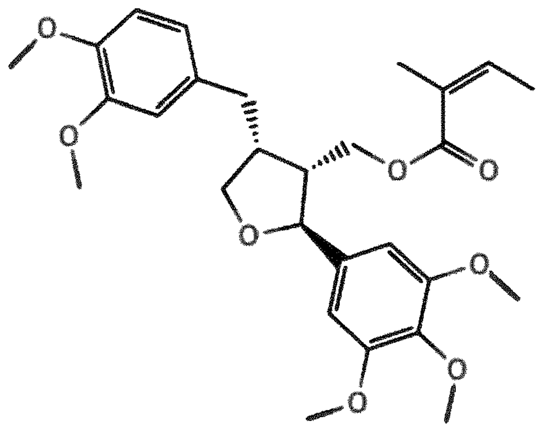
FIG. 2 Structural formula of derivatives of leoligin.
Figure 2:
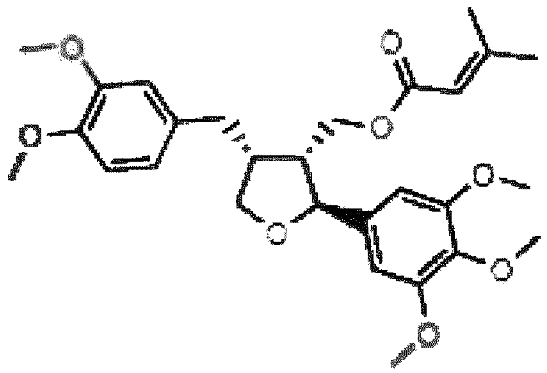
Figure 2:
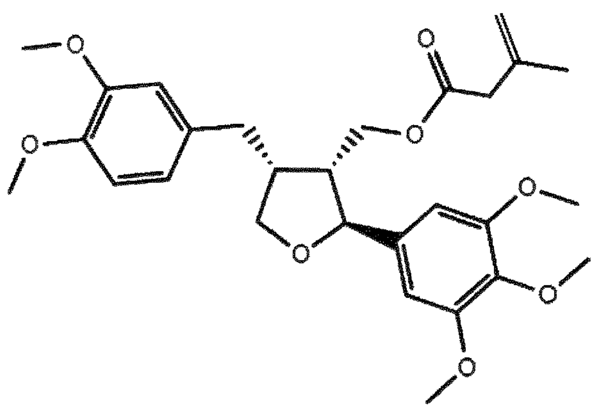
Figure 2:
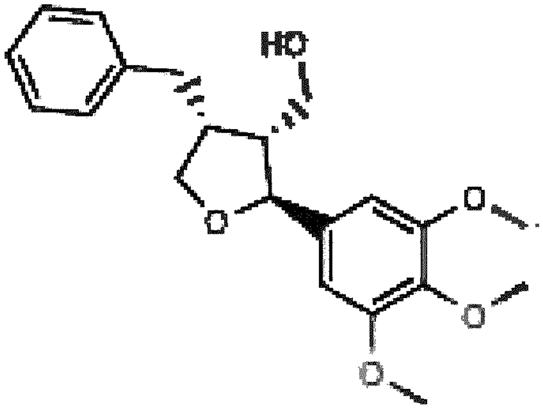
Figure 2:
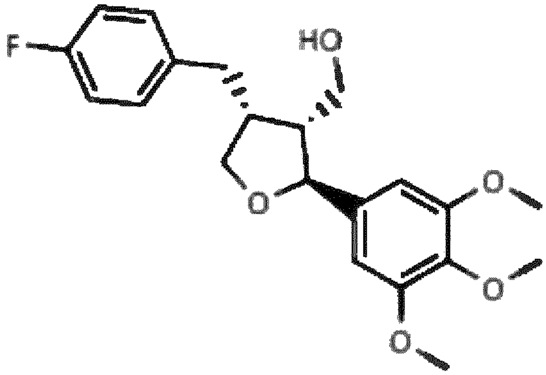
Figure 2:
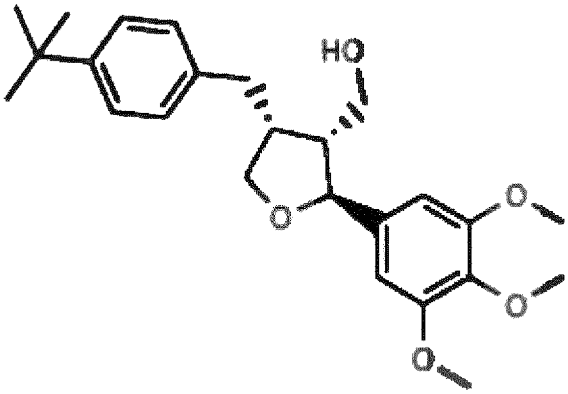
Figure 2:
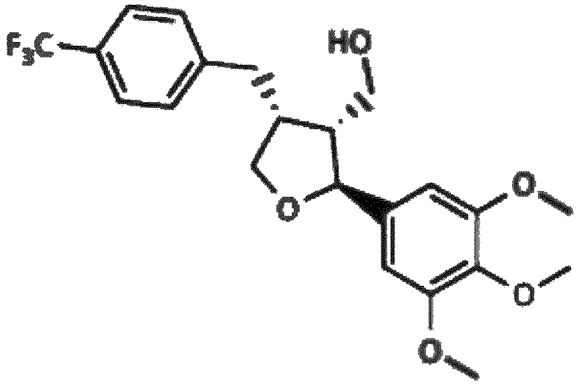
Figure 2:
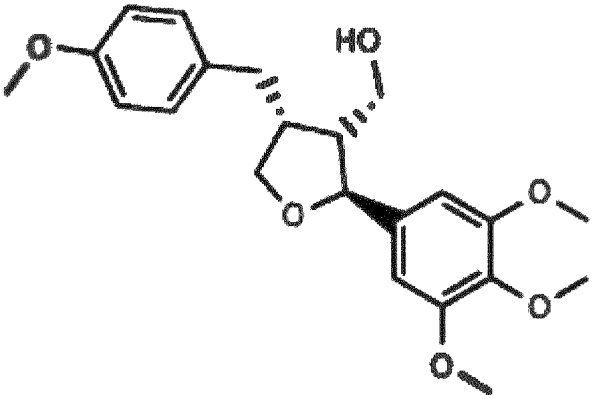
Figure 2:
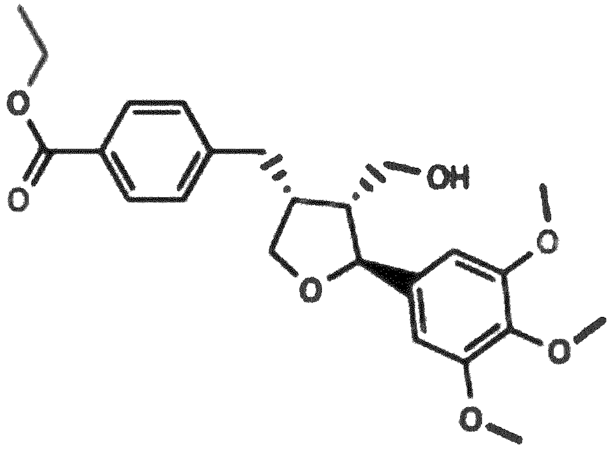
Figure 2:
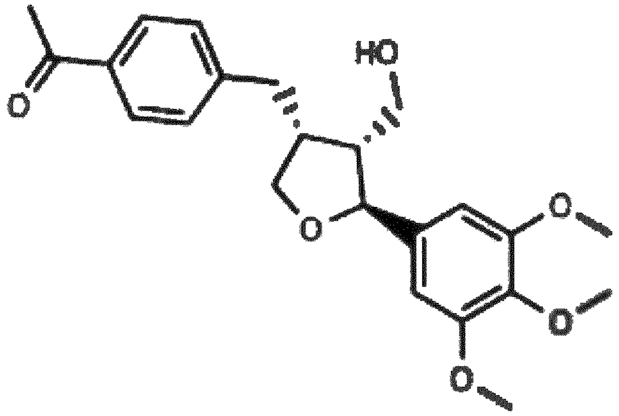
Figure 2:
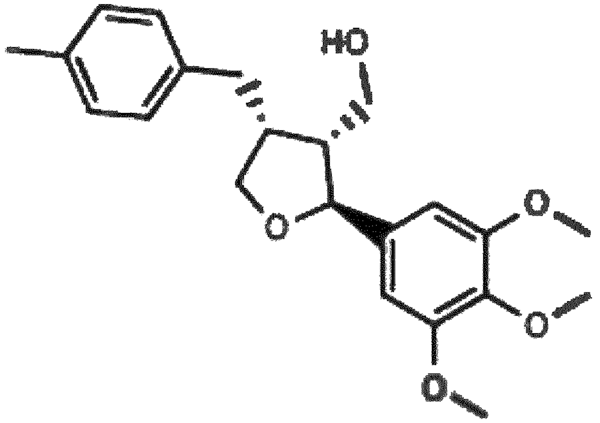
Figure 2:
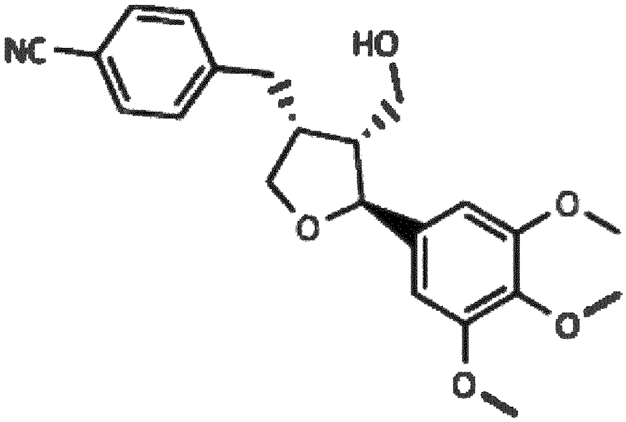
Figure 2:
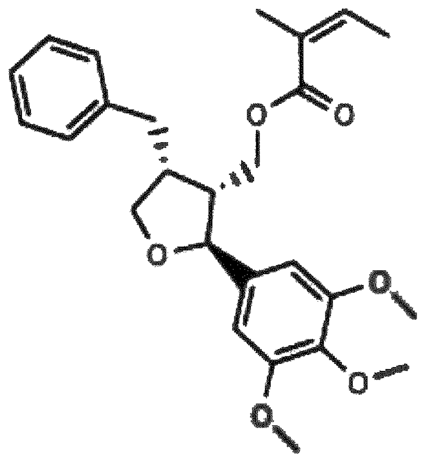
Figure 2:
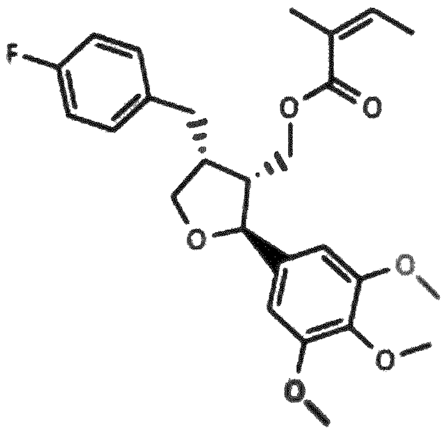
Figure 2:
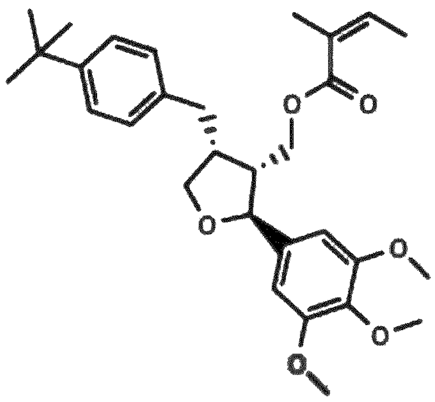
Figure 2:
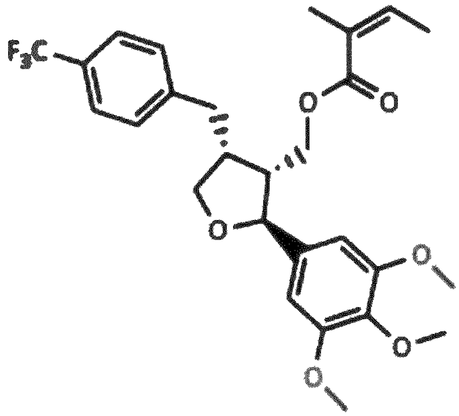
Figure 2:
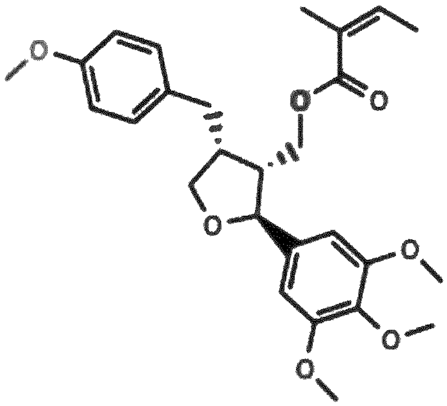
Figure 2:
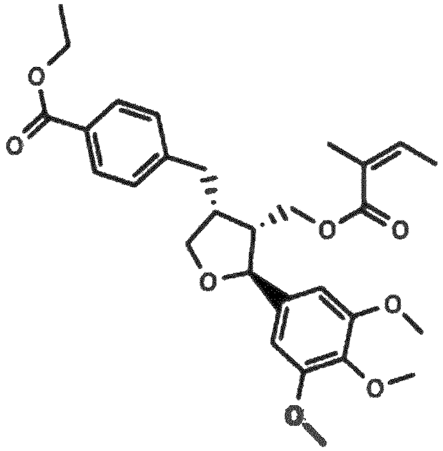
Figure 2:
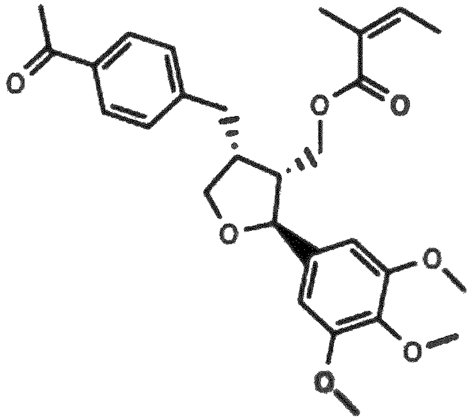
Figure 2:
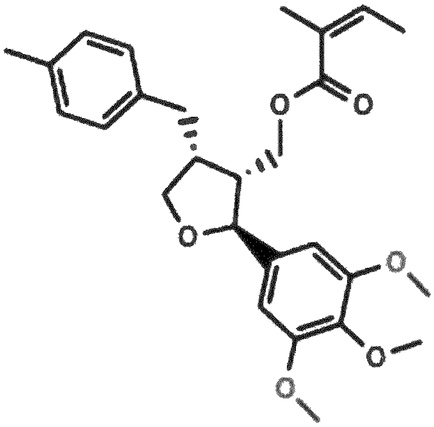
Figure 2:
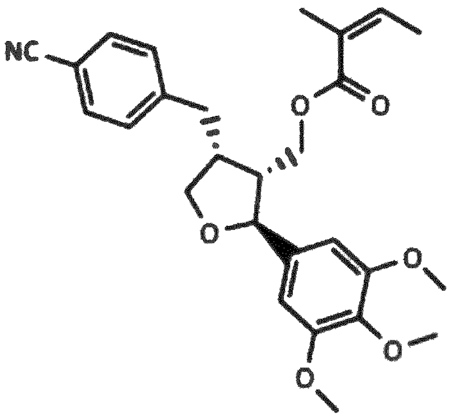
Figure 2:
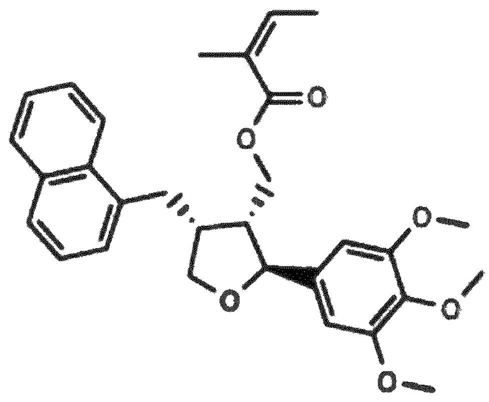
Figure 2:
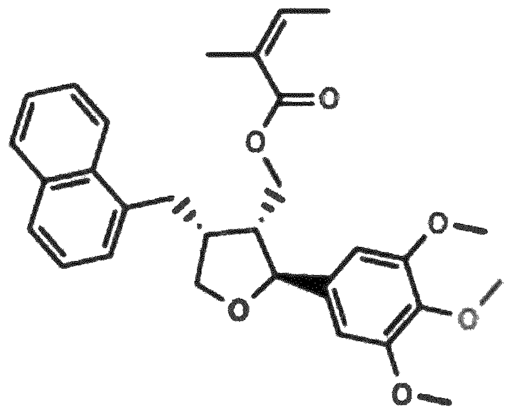
Figure 2:
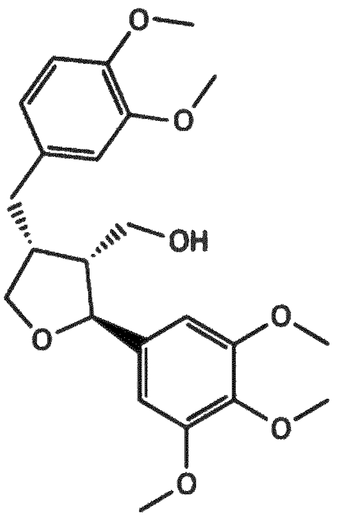
Figure 2:
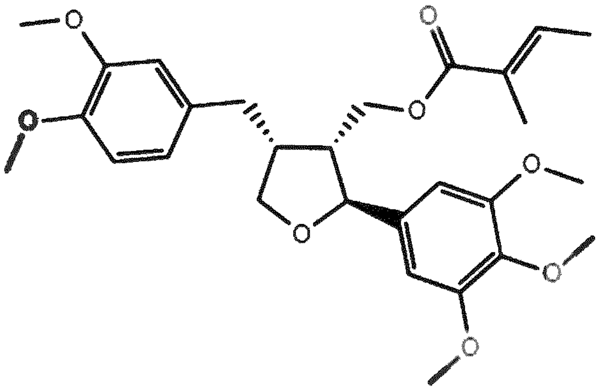
Figure 2:
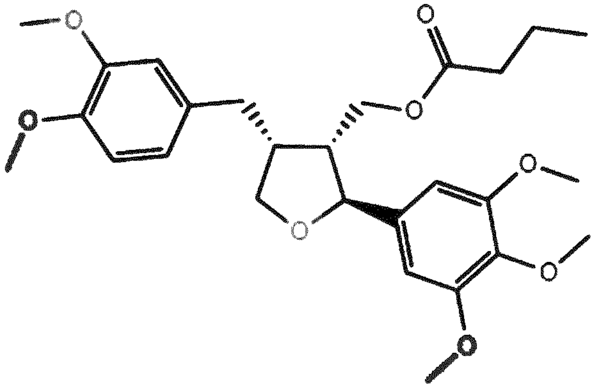
Figure 2:
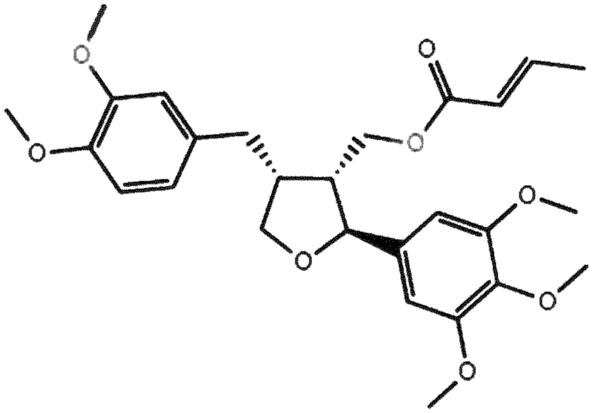
Figure 2:
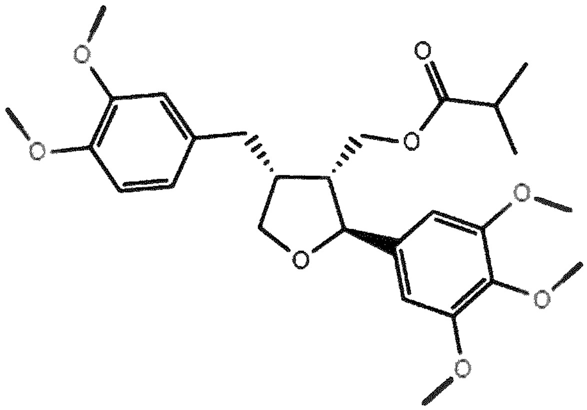
Figure 2:
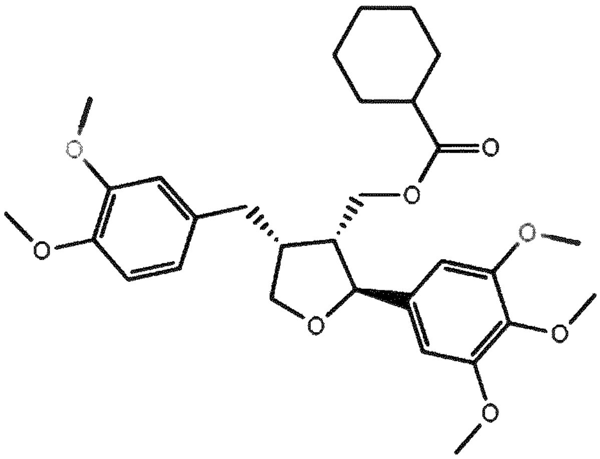
Figure 2:
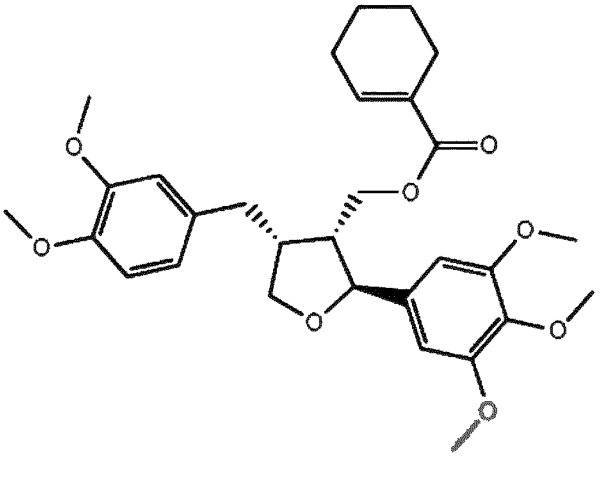
Figure 2:
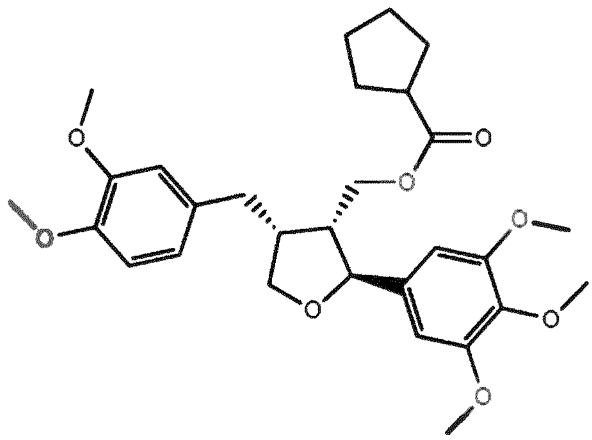
Figure 2:
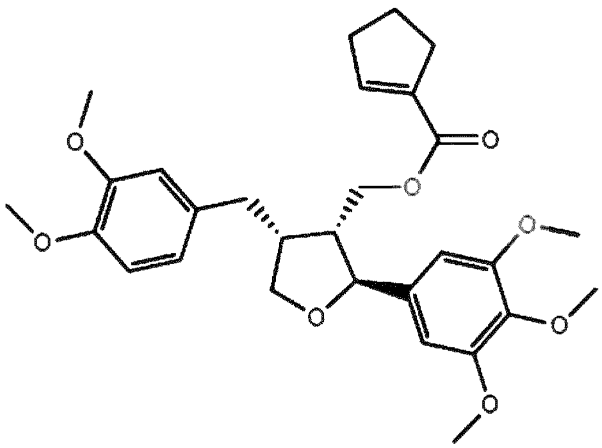
Figure 2:
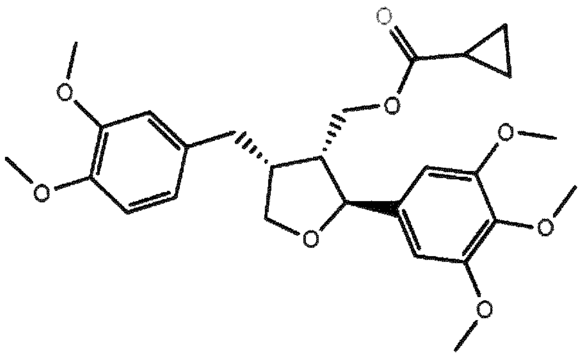
Figure 2:
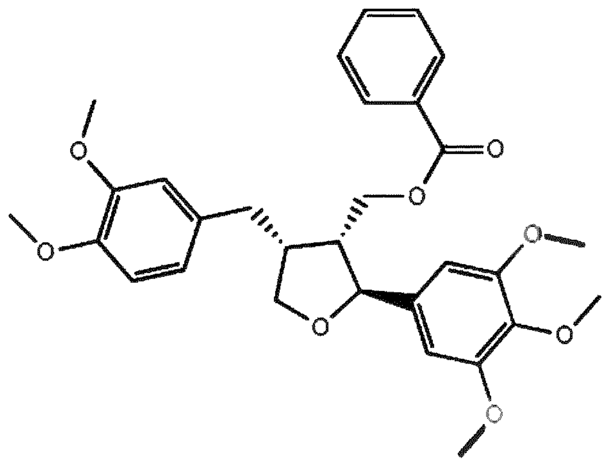
Figure 2:
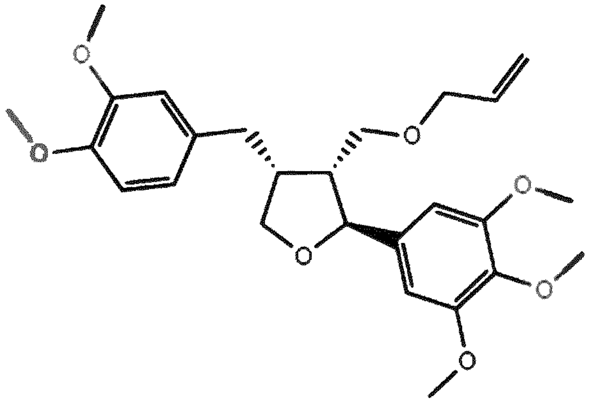

Unless indicated or defined otherwise, all terms used herein have their usual meaning in the art, which will be clear to the skilled person.

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

As used herein and in the claims, the singular form, for example "a", "an" and "the" includes the plural, unless the context clearly dictates otherwise.

Specifically provided herein is a formulation of leoligin or a derivative thereof in a therapeutically efficient amount for use in the treatment of a subject suffering from a condition associated with hypoxia, wherein the formulation is administered systemically, preferably through pulmonary, buccal and/or sublingual administration.

Leoligin (A) is a lignan, which was isolated from the roots of Edelweiss (*Leontopodium alpinum* Cass.). The IUPAC name for leoligin is: [(2S,3R,4R)-4-(3,4-dimethoxybenzyl)-2-(3,4-dimethoxyphenyl)tetrahydrofuran-3-yl]methyl (2Z)-2-methylbut-2-enoat.

Derivatives of leoligin include but are not limited to natural derivatives of leoligin, such as 5-methoxyleoligin (=[(2S,3R,4R)-4-(3,4-dimethoxybenzyl)-2-(3,4,5-trimethoxyphenyl)tetrahydro-furan-3-yl]methyl-(2 Z-2-methylbut-2-en-oate, and 5,5'-dimethoxyleoligin (=[(2S,3R,4R)-4-(3,4,5-trimethoxybenzyl)-2-(3,4,5-trimethoxyphenyl)tetrahydro-furan-3-yl]methyl-(2Z)-2-methylbut-2-en-oate. The chemical formula of 5-methoxyleoligin is $C_{28}H_{36}O_8$. Optically pure 5-methoxyleoligin is a furan lignin, which may for example be isolated from the roots of *Leontopodium* species, or synthesized via various synthetic pathways.

The present invention solves the above identified objective since it was surprisingly found that leoligin and derivatives thereof exhibit a beneficial effect in a medical setting. Specifically, leoligin has been shown to protect tissue from damage due to vascular obliteration or hypoxia and is able to prevent tissue damage upon systemic administration.

Specifically, the compound to be used in accordance with the present invention or the compound as comprised in the pharmaceutical composition or formulation of the present invention may be obtained from plants belonging to the genus *Leontopodium*, optionally followed by standard derivatization reactions. It is particularly preferred that the compounds provided herein may be obtained from *Leontopodium alpinum*, in particular *Leontopodium alpinum* Cass., which is commonly known under the trivial name "edelweiss". According to another nomenclature "edelweiss" may also be known under the scientific term "*Leontopodium nivale* subsp. *alpinum* (Cass.) Greuter". However, the terms "*Leontopodium alpinum* Cass" and "*Leontopodium nivale* subsp. *alpinum* (Cass.) Greuter" refer to the same plant species and merely reflect a regrouping of the species in botanical nomenclature. Accordingly, these terms can be used interchangeably in context of the present invention and any definitions and explanations given herein in respect of *Leontopodium alpinum* Cass. also applies to *Leontopodium nivale* subsp. *alpinum* (Cass.) Greuter, mutatis mutandis, and vice versa.

Of course, it is envisaged herein that the compounds to be used according to the present invention may be obtained from other *Leontopodium* species, including but not limited to commercial cultivars, such as *Leontopodium* hybrids.

Of course, the compounds provided herein may also be obtained from corresponding cell culture, cell suspension culture or a comparable in vitro cultivation technique, such as callus culture and the like. A person skilled in the art will be aware of corresponding means and methods for establishing and maintaining corresponding cultures. In a preferred embodiment of the invention, the cell culture is derived from roots of *Leontopodium* species described herein above, in particular *Leontopodium alpinum* (edelweiss). Most preferably, the cell culture is derived from hairy roots.

Based on his general knowledge and the teaching provided herein a skilled person is readily in the position to obtain the compounds to be used herein, in particular leoligin, from *Leontopodium* species. Generally, the person skilled in the art is capable of preparing an extract from plants belonging to the genus *Leontopodium* by standard techniques. A preferred method for extracting these compounds from the roots of *Leontopodium alpinum* is for example provided in US2014/0371306A1. An artisan will be aware how to adapt this protocol for extracting the compounds from further *Leontopodium* species and in particular from roots of these plants. A skilled person will also be aware of alternative protocols to be used in this context.

The term extract is well known in the art and used accordingly herein. For example, this term may refer to preparations of fluid consistence (fluid extracts and tinctures), semisolid consistence (viscous extracts, syrup concentrate) or solid consistence (dried extracts), which are usually prepared using fresh or dried plant material.

The extract obtained from *Leontopodium* species is an extract that is received by the use of an organic or nonorganic solvent. Suitable solvents are hexane, heptane, petroleum benzene, acetone, chloroform, dichloromethane, ethyl acetate, diethylether, liquid carbon dioxide, ethanol, ternary butyl methyl ether (tBMe) and mixtures of water and alcohol. The extract may be obtained by extracting the plant material, in particular roots, with any of the solvents separately. It is further possible to subsequently extract the obtained extract with a second solvent or mixtures of different solvents. An exemplary, non-limiting solvent to be used in a first extraction step is hexane. However, any of the above solvents can be used in such a first extraction step. This first extraction step may be followed by (a) subsequent second (or further) extraction step with at least one of the above exemplary solvents, e.g. dichloromethane, chloroform or ternary butyl methyl ether (tBMe). Extraction of the compounds disclosed herein, in particular leoligin and/or its (di)methoxy-derivative(s)) is also illustrated in US2014/0371306A1.

Preferably, dichloromethane and methanol are used as extraction solvents. In subsequent extraction, it is preferred that the compounds are first extracted with n-hexane, followed by a subsequent extraction with dichloromethane, chloroform or tBMe. The lignan content can be increased by a second or further extracting steps. Also, the use of chromatographic methods, such as Sephadex-LH20-column chromatography and in particular silica gel column chromatograph is advantageous in this context.

Further chromatographic methods to increase the content of leoligin and/or its (di)methoxy-derivative(s)) can be used in addition or in the alternative to the above-described methods. Exemplary, non-limiting chromatographic methods to be used in this context are reversed phase column chromatography or (semi)-preparative HPLC using water/acetonitrile mixtures or comparable solvent mixtures known in the art. Alternatively, techniques of liquid-liquid extractions (discontinuous or continuous methods) can be used to increase the content of leoligin and its derivatives. An exemplary liquid-liquid extraction is high speed counter current chromatography using a solvent system of two not mixable solvents.

The preparation of the basic extract of *Leontopodium* species, in particular *Leontopodium alpinum*, may comprise mechanical pulping, sonication, use of mortars and pestles, freeze-thawing cycles, use of blenders (like Waring Blenders, Polytron), liquid homogenization and maceration (see also appended examples), or e.g. Dounce homogenization, Potter-Elvehjem, French Press etc. However, the extracts may also be obtained by disrupting the cells and cells from the *Leontopodium* species by any mechanical/physical or chemical means, like by use of detergents.

The cells and plants to be employed in order to obtain the basic extract may be cells of natural origin as well as cultured cells or plants. It is preferred herein that the cells or plants and in particular roots of the plants are dried before mechanical disruption/maceration as described herein above. The cells or plants may be air dried, lyophilized (freeze-dried) or, though less preferred, dried in an oven. It is preferred herein that the "cell(s)" and "plant(s)" to be used as a basic material are fresh, i.e. harvested shortly before the extract is prepared. Nonetheless, it is possible to store the basic material before its use in the preparation of the extract. For example, the basic material may be lyophilized (freeze-dried) or simply frozen and stored at low temperatures, e.g. at about −20 to −30° C., or as low as −80° C.

Preferably, the extract is an enriched extract, i.e. contains leoligin and/or its derivatives in a high amount. Such an enriched extract can, for example, be obtained by taking advantage of silica gel chromatography. Silica gel column chromatography is well known in the art and described in detail in standard textbooks, such as "Preparative Chromatography Techniques" by Hostettmann, K. Marston, Andrew Hostettmann, Maryse, Springer-Verlag GmbH, 2007, 260 p.

In an alternative embodiment, the compounds to be used herein may also be synthesized. An exemplary synthetic pathway of leoligin and derivatives thereof, such as 5-methoxyleoligin, is shown in e.g., US2014/0371306A1 and US2017/0157301A1. The shown synthetic pathway might be adapted by a change of the corresponding educts to obtain other compounds of the present invention. A skilled person will be aware of methods of synthesizing the compounds of the present invention, in particular 5-methoxyleoligin, or may deduce corresponding methods e.g. from Li Hong Hu, *J. Nat. Prod.* 68, 342-8. (2005) or Linder et al. *Chem. Sci.* 10(22):5815-5820 (2019).

According to a specific embodiment, key steps of the synthetic production of leoligin and derivatives thereof, as described in Linder et al., involve (i) establishing an enantiomerically pure status upon lipase mediated kinetic resolution; (ii) formation of a tetrahydrofuran ring system upon diastereoselective radical cyclization; (iii) regio- and stereoselective arylation via hydroboration and subsequent Suzuki-Miyaura cross-coupling in a single-operation cascade and, finally, (iv) esterification employing a modified Mitsunobu protocol (Linder et al. *Chem. Sci.* 10(22):5815-5820 (2019)).

As used herein, the term "patient" or "subject" refers to both, humans and other animals, particularly warm-blooded animals and/or mammals. Thus, the methods and compositions described herein are applicable to both human therapy and veterinary applications. Preferably, the patient is a mammal. A "subject" mammal can include, but is not limited to, a human or non-human mammal, such as a primate, bovine, equine, canine, ovine, feline, or rodent. Preferably, the patient or subject is a human.

The term "treatment" relates to any treatment which improves the health status, reduces or inhibits unwanted tissue damage and/or prolongs and/or increases the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

As used herein, "preventing" or "prevention" of a disease, disorder or condition refers to the reduction of the occurrence of the disorder or condition in a treated subject relative to an untreated control subject, or delays the onset or reduces the severity of one or more symptoms of the disorder or condition relative to the untreated control subject.

The terms "protect", "prevent", "prophylactic", "preventive", or "protective" specifically relate to the prevention and/or treatment of the occurrence and/or the propagation of tissue damage, e.g. caused by hypoxia, in an individual. For example, a prophylactic administration of a leoligin composition according to the present invention can protect the receiving individual from the development of tissue damage. For example, a therapeutic administration of leoligin or a derivative thereof, e.g. by administering a composition of the present invention, can stop the development of tissue damage or further tissue damage, e.g. in the event of a stroke or myocardial infarction.

As explained above, it is a particular advantage of the invention that the composition does not have to be administered directly to the tissue, which is to be protected, in an invasive manner, such as for example injection into the heart muscle. Instead, leoligin or a derivative thereof is administered systemically to a subject or patient in need thereof. The inventors have surprisingly found that leoligin administered systemically, such as via the pulmonary route, is capable of preventing tissue damage in a hypoxic environment.

The pharmaceutical compositions or pharmaceutically acceptable formulations described herein comprise leoligin or a derivative thereof as active ingredient in an effective amount. The leoligin compounds to be used in accordance with the present invention may be obtained from *Leontopodium* plants as described herein above and/or chemically synthesized.

The pharmaceutical composition described herein, will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations.

The skilled person knows that the effective amount of pharmaceutical composition administered to an individual will, inter alia, depend on the nature of the compound. For example, if said compound is leoligin the total pharmaceutically effective amount of composition administered systemically as described herein will be in the range of about 0.01 mg/kg/day [minimum dose] to 10 mg/kg/day [maximum dose] of patient body weight, although, as noted above, this will be subject to therapeutic discretion.

More preferably, this dose is at least 0.25 mg/kg/day, and most preferably for humans between about 0.05 and 5 mg/kg/day.

The length of treatment needed to observe changes and the interval following treatment for responses to occur may vary depending on the desired effect. The particular amounts may be determined by conventional tests which are well known to the person skilled in the art.

Pharmaceutical compositions of the invention preferably comprise one or more pharmaceutically acceptable carriers. As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier is selected for administration by the selected route of administration. The use of such media and agents for pharmaceutically active substances is well known in the art (Rowe R. C. et al, Handbook of Pharmaceutical Excipients, 2012, 7th edition, Pharmaceutical Press, London UK). Except insofar as any conventional media or agent is incompatible with the active compound, use thereof in the pharmaceutical compositions of the invention is contemplated.

Non-limiting pharmaceutically suitable materials that may be incorporated in pharmaceutical preparations of the present invention include solubilizing/diluting agents, antioxidants, enteric coatings, absorption enhancers, pH adjusting agents and buffers, dispersing agents, coatings, antibacterial and antifungal agents, absorption delaying agents, osmolarity adjusters, isotonic agents, preservative agents, stabilizers, surfactants, thickening agents, solvents, co-solvents, emollients, coloring agents, wetting agents and ligands/pilot/targeting molecules. Methods for preparing appropriate formulations are well known in the art.

As used herein, the term "systemic administration" refers to a route of administration of a product, specifically the compositions and formulations described herein, into the circulatory system of a subject or patient. Specifically, the term "systemic administration" as used herein refers to administration via the respiratory tract, buccal administration, sublingual administration or parenteral administration.

As used herein, the term "systemic administration" preferably excludes enteral administration, i.e. absorption of the drug through the gastrointestinal tract.

The term "sublingual administration", synonymous with "sublingual delivery", as used herein refers to the pharmacological route of administration by which substances diffuse into the blood through tissues under the tongue.

The term "buccal administration", synonymous with "buccal delivery", as used herein refers to a topical route of administration by which drugs held or applied in the buccal area (in the cheek) diffuse through the oral mucosa and enter directly into the bloodstream.

Specifically, formulations for sublingual administration comprise tablets, capsules, bars, lozenges or granules having a size so small (generally not exceeding 9-10 mm diameter) that they can be placed in the sublingual cavity of the mouth, whereas formulations for buccal, peribuccal or orobuccal administration comprise tablets, capsules, bars, lozenges or granules having a greater size, which are dissolved or chewed in the oral cavity.

In both cases, sublingual or buccal administration, the delivery system consists in placing a given product (tablet, lozenge etc.) inside the oral cavity and waiting until it is dissolved after a short time, generally a few minutes. It is a form of very fast intake, wherein the product comes into contact with the mucous membrane, and spreads, dissolving, evenly in the epithelium under the tongue, an area full of blood vessels, entering into the circulatory system, i.e. into the blood, much faster than oral administration (where the tablet is swallowed). Such an effect is explained in view of the fact that the oral haematic system discharges the active ingredient in the superior vena cava thus avoiding the portal venous system responsible of the known effect of first pass splanchnic metabolism, thereby improving systemic bioavailability.

In a specific embodiment, leoligin or the derivative thereof, is provided as orosoluble and/or effervescent formulation for sublingual, or buccal or orobuccal or peribuccal use, containing leoligin or a derivative thereof, specifically 5-ML, in combination with physiologically acceptable carriers and/or excipients.

The orosoluble and/or effervescent compositions of the present invention are preferably characterized by the fact of having a high palatability, which guarantees easy administration in the oral cavity. Said high palatability (meant as very pleasant taste) also provides for a lower impulse to swallow, which helps to improve the absorption rate and bioavailability of the active ingredient due to a longer period of permanence of the composition in the oral cavity.

The orosoluble and/or effervescent compositions of the present invention can therefore be formulated in tablets, lozenges, powders, capsules and/or granules, preferably in the form of an orosoluble and/or effervescent tablet.

According to the present invention the term "orosoluble" refers to a composition capable of melting immediately, releasing the active ingredient contained therein when in contact with the oral mucosa.

In this way, the active ingredient can be absorbed directly into the oral mucosa, thus bypassing the hepatic system. According to the invention, the term orosoluble is therefore used to indicate compositions to be introduced in the oral cavity.

The compositions of the present invention can be formulated with further excipients, such as sweeteners or flavorings (added to improve the organoleptic characteristics of the products); antioxidants-antimicrobials (used to prolong the shelf life of the product); gliding agents (used to improve the flow properties of the granules or powder and thus to facilitate the filling of the matrix in a homogeneous manner, allowing to achieve uniform tablets by weight); solubilizing agents (for favouring the solubilisation of the composition); and/or pH regulating agents.

The excipients of the conventional type most commonly used are: lactose, glucose, saccharose, mannite (or mannitol), kaolin, talc, bentonite, titanium dioxide, xylitol, maltitol, sorbitol, sucralose, acesulfame K, aspartame, neohesperidin, fructose, dextrose, maltose, "spray-dried" malt, aspartate sodium, maltodextrin, sodium chloride, hydroxypropylmethylcellulose, erythritol, citrus extract, silica gel, vegetable fibres (as for example, the pea fibre), flavouring agents and aromas, such as mint flavour (peppermint, spearmint, fresh mint), anethole of star anise, vanilla, sage, liver, chicken, grapefruit, peach, orange, lemon or lime, sodium glutamate and fish flour.

To obtain the orosoluble for, the compositions of the invention are for example formulated using the excipients described above.

More preferably, the orosoluble compositions according to the invention are formulated with magnesium oxide, magnesium hydroxide, alginic acid, stearic acid, hydrogenated vegetable oils (palm, oleic, behenic), cocoa butter, cocoa mass, xylitol, maltitol, sorbitol, mannitol, sucralose, acesulfame K, cyclamate, aspartame, sucrose, neohesperidin, fructose, dextrose, maltose, spray dried malt, aspartate sodium, maltodextrin, inositol, inulin, chitosan, beer yeast or a mixture of two or more of the foregoing excipients. In particular, in order to obtain the orosoluble form, said excipients are present in the compositions of the invention in an amount from 20% to 95% by weight, relative to the total weight of the formulation.

Further provided herein is a pharmaceutical liquid composition for buccal or sublingual administration comprising leoligin or a derivative thereof, an alcoholic solvent, and, optionally, one or more pharmaceutically acceptable carriers and/or excipients.

The liquid pharmaceutical composition according to the present invention is in the form of solution, suspension, nano-suspension, emulsion, micro-emulsion, multiple emulsion and the like meant for administration through oral mucosa preferably, in the form of solution.

Another embodiment of the present invention relates to pharmaceutical liquid spray composition for buccal or sublingual administration consisting essentially of leoligin or a derivative thereof, and an alcoholic solvent.

In another preferred embodiment, the present invention relates to pharmaceutical liquid spray compositions for buccal or sublingual administration consisting of leoligin or a derivative thereof, an alcoholic solvent and water.

In a specific embodiment, systemic administration of the leoligin or derivative thereof may be via parenteral administration, e.g. by intramuscular self-injection.

In cases where parenteral administration is elected as the route of administration, pharmaceutical compositions of the present invention may be provided to patients in combination with additional pharmaceutically acceptable sterile aqueous or non-aqueous solvents, suspensions or emulsions. Formulations to be used for in vivo administration are preferably sterile. This is readily accomplished, for example, by filtration through sterile filtration membranes.

Pharmaceutically acceptable carriers for parenteral formulations include sterile aqueous solutions or dispersions and sterile powders for the extemporaneous preparation of sterile injectable solutions or dispersion. Aqueous solvents include water, alcohol, specifically ethanol, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils.

Intravenous vehicles may include fluid and nutrient replenishers, electrolyte replenishers, such as those based upon Ringer's dextrose, and the like.

Formulations suitable for oral administration, specifically buccal or sublingual administration, can consist of liquid solutions, such as an effective amount of active agent(s) suspended in diluents/solubilizers, such as water, vegetable or animal oils, saline or PEG 400; capsules such as soft shell capsules, sachets or tablets, each containing a predetermined amount of the active ingredient, as liquids, solids, granules or gelatin; suspensions in an appropriate liquid; and suitable emulsions.

Aqueous solutions suitable for oral use, specifically buccal or sublingual delivery, are prepared by dissolving the active compound(s) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. Examples of non-aqueous solvents are alcohol, benzyl benzoate, butyl alcohol, polyethylene glycol, propylene glycol, N,N-dimethylacetamide, ethyl oleate, oleyl oleate, glyceryl trioleate, glyceryl dioleate, glyceryl monooleate, cetyl alcohol, stearyl alcohol, capric acid, undecenoic acid, undecanoic acid, lauric acid, oleic acid, synthetic glycerides of saturated fatty acids with 8 to 12 carbon atoms, polyoxyethylene derivatives of glycerol, bees' wax, glycerin, mineral oil, vegetable oil such as but not limited to corn oil, cottonseed oil, peanut oil, canola oil, sesame oil, safflower oil, soybean oil, arachis oil, castor oil, linseed oil, soya bean oil, sunflower seed oil, olive oil, fish liver oil, and any combination thereof.

Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Cellulose acetate phthalate concentrations generally used are 0.5-9.0% of the core weight. The addition of plasticizers improves the water resistance of this coating material, and formulations using such plasticizers are more effective than when cellulose acetate phthalate is used alone. Cellulose acetate phthalate is compatible with many plasticizers, including acetylated monoglyceride; butyl phthalybutyl glycolate; dibutyl tartrate; diethyl phthalate; dimethyl phthalate; ethyl phthalyl ethyl glycolate; glycerin; propylene glycol; triacetin; triacetin citrate; and tripropionin. It is also used in combination with other coating agents such as ethyl cellulose, in drug controlled-release or time-release preparations.

Generally, the formulations described herein are prepared by contacting the components of the pharmaceutical composition uniformly and intimately with liquid carriers or finely divided solid carriers or both. Then, if necessary, the product is shaped into the desired formulation. The carrier may be a solution that is isotonic with the blood of the recipient. Examples of such carrier vehicles include water, saline, Ringer's solution, and dextrose solution. Non-aqueous vehicles, such as fixed oils and ethyl oleate, are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

According to a preferred embodiment, leoligin or its derivatives are administered as inhalable powder. In spray and aerosol compositions, leoligin is delivered to the mouth in a dosed amount through a nozzle or orifice. The composition may be delivered through a pump spray, a pressurized spray or as an aerosol. Moreover, it is easy to apply and it is possible to ensure the delivery of the composition to the oral mucosa and/or airways.

For example, leoligin or its derivatives can be formulated for delivery into the upper respiratory system. Exemplary formulations include nasal, bronchial, oral, and pulmonary formulations. In a specific embodiment, a composition comprising leoligin as described herein is formulated as an aerosol. The aerosol can be a liquid or powdered aerosol. In some embodiments, the composition contains one or more pharmaceutically acceptable excipients such as glycerin. The composition can contain 0.01%-20% w/v of the esterified green tea polyphenol and 10% to 20% glycerol.

The composition, shape, and type of dosage forms of leoligin as described herein will typically vary depending on their use. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

In a preferred embodiment, leoligin and its derivatives are delivered to oral, nasal, or bronchial tissue in a suitable topical dosage form.

Nasal spray drug products contain therapeutically active ingredients dissolved or suspended in solutions or mixtures of excipients in non-pressurized dispensers that deliver a spray containing a metered dose of the active ingredient. The dose can be metered by the spray pump or could have been pre-metered during manufacture. A nasal spray unit can be designed for unit dosing or can discharge up to several hundred metered sprays of formulation containing the drug substance. Nasal sprays are applied to the nasal cavity for local and/or systemic effects.

Inhalation solution and suspension drug products are typically aqueous-based formulations that contain therapeutically active ingredients and can also contain additional excipients. Aqueous-based oral inhalation solutions and suspension must be sterile. Inhalation solutions and suspensions are intended for delivery to the lungs by oral inhalation for local and/or systemic effects and are to be used with a specified nebulizer.

An inhalation spray drug product consists of the formulation and the container closure system. The formulations are typically aqueous based and must be sterile. Inhalation sprays are intended for delivery to the lungs by oral inhalation for local and/or systemic effects. Inhalation spray drug products containing the disclosed compositions can also contain additional excipients.

Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Examples of sprayable aerosol preparations include but are not limited to metered dose inhalers, dry powder inhalers, and nebulizers. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

In some embodiments, the effect of leoligin, leoligin derivatives and compositions thereof on a subject is compared to a control. For example, the effect of the composition on a particular symptom, pharmacologic, or physiologic indicator can be compared to an untreated subject or the condition of the subject prior to treatment. In some embodiments, the symptom, pharmacologic, or physiologic indicator is measured in a subject prior to treatment, and again one or more times after treatment is initiated. In some embodiments, the control is a reference level, or an average determined from measuring the symptom, pharmacologic, or physiologic indicator in one or more subjects that do not have the disease or condition to be treated (for example, healthy subjects). In some embodiments, the effect of the treatment is compared to a conventional treatment that is known in the art.

According to a specific aspect, the present invention relates to the use of crystalline leoligin or crystalline derivatives of leoligin as a medicament in the light of the pharmaceutical efficacy of the anhydrous form according to the invention. To prepare a medicament which can be inhaled, particularly an inhalable powder, which contains the anhydrous, crystalline leoligin described by the present invention, methods known from the prior art may be used. In this respect, reference is made, for example, to the teaching of DE-A-179 22 07. Accordingly, a further aspect of the present invention relates to inhalable powders characterized in that they contain anhydrous, crystalline leoligin or its derivatives.

Preferably, the following physiologically acceptable excipients are used in an inhalable powder formulation: monosaccharides (e.g. glucose or arabinose), disaccharides (e.g. lactose, sucrose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates.

The conducting airways provide a high filter capacity (up to 90%). Inhaled substances are deposited on the mucus which is secreted by goblet and submucosal gland cells and consists of mucin. Ciliated cells cause pro pulsation, and this leads mucus to be transported upward and out of the lung for gastric clearance and metabolism. The second and major mechanism is phagocytosis by lung-surface macrophages which patrol the air space of the alveoli and can incorporate particles. Particles smaller than 200 nm are not cleared by this mechanism.

Therefore, according to a specific embodiment, the inhalable powders as described herein comprise a small average particle size of about 200 nm or less.

Within the scope of the inhalable powders according to the invention the excipients which are characterized in that they contain leoligin or its derivatives have a maximum average particle size of up to 200 nm, preferably between 10 and 150 nm, most preferably between 20 and 100 nm. It may sometimes seem appropriate to add finer excipient fractions with an average particle size of 1 to 9 nm to the excipients mentioned above. These finer excipients are also selected from the group of possible excipients listed hereinbefore. Further specific inhalable powders containing the leoligin or its derivatives according to the invention are characterized in that the excipient consists of a mixture of coarser excipient with an average particle size of from 5 to 50 μm, more preferably 10 to 25 μm, and finer excipient with an average particle size of 0.1 to 5 μm, more preferably 0.2 to 1 or 2 μm. The term average particle size here denotes the 50% value from the volume distribution measured with a laser diffractometer by the dry dispersion method. Inhalable powders wherein the proportion of finer excipient in the total quantity of excipient is 3 to 15%, more preferably 5 to 10%, are preferred.

According to a specific embodiment, carrier particles are used to transport leoligin or derivatives thereof. Carrier particles can be microparticles which are relatively large in size, e.g. bigger than about 5 μm, and low in density, e.g. comprising a density of less than about 0.4 g/cm$^3$. Because of their size, such microparticles can escape impaction in the upper airways and reach deeper areas of the lungs, typically the central and distal tract, and they escape phagocytosis of alveolar macrophages more easily.

Specific examples of carrier particles include polymeric nanoparticles, micelles, liposomes, solid lipid nanoparticles, dendrimers and PEGylated nanoparticles.

According to a specific embodiment, particle-loaded gas is inhaled. Examples of the gas are particle-loaded sulphox, comprising 80% sulfur hexafluoride and 20% oxygen, and particle-loaded heliox, comprising 80% helium and 20% oxygen. Preferably, particle-loaded sulphox is used. It is beneficial that the particle-loaded gas is heavier than air, so that particles penetrate deeper into the lungs.

One possible method of preparing inhalable powders as described herein is discussed in more detail hereinafter. After the starting materials have been weighed out, first the excipient mixture is prepared from the defined fractions of the coarser excipient and finer excipient. Then the inhalable powders according to the invention are prepared from the excipient mixture and the active substance, specifically leoligin or its derivatives. If the inhalable powder is to be administered by means of inhalants in suitable inhalers, the preparation of the inhalable powders is followed by the production of the capsules containing the powder.

According to a specific embodiment, the inhalable powders described herein are prepared by mixing the coarser excipient fractions with the finer excipient fractions and subsequently mixing the resulting excipient mixtures with the active substance, specifically leoligin or its derivatives. In order to prepare the excipient mixture, the coarser and finer excipient fractions are placed in a suitable mixing container. The two components are preferably added through a screening granulator with a mesh size of 0.1 to 2 mm, most preferably 0.3 to 1 mm, even more preferably 0.3 to 0.6 mm. Preferably the coarser excipient is put in first and then the finer excipient fraction is added to the mixing container. In this mixing process the two components are preferably added batchwise, with half the coarser excipient being put in first followed by finer and coarser excipient added alternately. It is particularly preferable when preparing the excipient mixture to screen the two components in alternate layers. Preferably this screening of the two components takes place in 15 to 45, more preferably in 20 to 40 alternate layers. The mixing of the two excipients may take place while the two components are being added. However, it is preferably not done until the layers of ingredients have been added.

After the preparation of the excipient mixture, this and the active substance are placed in a suitable mixing container. The two components are preferably added through a screening granulator. Preferably the excipient mixture is put in first and then the active substance is added to the mixing container. The mixing of the excipient mixture with the active substance may take place while the two components are being added. However, it is preferably not done until the layers of ingredients have been added.

The powder mixture thus obtained may optionally be passed through a screening granulator once again or several times more and then subjected to another mixing operation each time.

The inhalable powders obtained by the above method preferably contain about 25 to 95% leoligin or its derivatives in admixture with a physiologically acceptable excipient. Specifically, the inhalable powder as described herein comprises about 30, 35, 40, 45, 50, 55, 60, 65, 70, 75, 80, 85, or 90% of leoligin or its derivatives. Preferred are inhalable powders which contain 50 to90% of leoligin or its derivatives in admixture with a physiologically acceptable excipient.

According to the invention, any pharmaceutically acceptable salts of leoligin or its derivatives may be used for the formulations described herein. When the term leoligin salt is used within the scope of the present invention, this is to be taken as a reference to leoligin. A reference to leoligin corresponds to the free ammonium cation. The leoligin salt accordingly contains an anion as the counter-ion. Leoligin salts which may be used within the scope of the present invention are preferably compounds which contain, in addition to leoligin as counter-ion (anion), chloride, bromide, iodide, methanesulfonate, p-toluenesulfonate, and/or methylsulfate.

The concentration of the leoligin salt based on the proportion of leoligin or its derivatives in the finished pharmaceutical preparation depends on the therapeutic effect sought.

Other pharmacologically acceptable adjuvants may be added to the formulation according to the invention. By adjuvants and additives are meant, in this context, any pharmacologically acceptable and therapeutically useful substance which is not an active substance, but can be formulated together with the active substance in the pharmacologically suitable solvent, in order to improve the qualities of the active substance formulation. Preferably, these substances have no pharmacological effects or no appreciable or at least no undesirable pharmacological effects in the context of the desired therapy. The adjuvants and additives include, for example, other stabilizers, complexing agents, antioxidants, and/or preservatives which prolong the shelf life of the finished pharmaceutical formulation, flavorings, vitamins, and/or other additives known in the art. The additives also include pharmacologically acceptable salts such as sodium chloride, for example.

The preferred excipients include antioxidants such as ascorbic acid, for example, provided that it has not already been used to adjust the pH, vitamin A, vitamin E, tocopherols, and similar vitamins or provitamins occurring in the human body.

Preservatives can be added to protect the formulation from contamination with pathogenic bacteria. Suitable preservatives are those known from the prior art, particularly benzalkonium chloride or benzoic acid or benzoates such as sodium benzoate in the concentration known from the prior art.

In one embodiment, the present invention relates to a medical device comprising, containing or having been contacted with a compound as described herein, i.e. leoligin and its derivatives.

Typical devices useful for the administration of leoligin or its derivatives are nebulizers. Nebulizers differ in the force used to generate the aerosol from the respective liquid. They generate 1-5 μm droplets. In jet nebulizers, air stream moves through a small capillary tube at high velocity creating a low pressure that drives the liquid to be aerosolized up to the capillary tube. A compressor is needed to generate the aerosol. Ultrasonic nebulizers create sound waves due to the vibration of piezoelectric crystals at high frequency. Ultrasonic nebulizers need an electric supply for charge. Variables to be considered to admit an accurate and consistent dose are:

Volume of drug solution that is loaded in the device,

Dead volume,

Viscosity of the drug solution,

Air flow and pressure in case of jet nebulizer, and

Tubing, mask ore mouthpiece.

However, the formulation according to the invention can also be administered using other devices such as for example jet-stream inhalers, pressurized metered dose inhalers and dry powder inhalers.

Pressurized metered-dose inhalers are the most common used to treat respiratory diseases. The metering valve is designed to deliver a precise aerosol amount (20-100 μL) each time the device is activated. Drug formulations can be solutions or suspensions in a single propellant mixture and may include excipients such as ethanol or surfactants to solubilize the drug or stabilize a drug suspension. Ideally, propellants should be nontoxic, non-flammable, and compatible with the formulation and provide consistent vapor pressure during the entire life of the product.

Dry powder inhalers are portable devices that require minimum patient coordination between breathing and actuation of the device to deliver powder medications. Drug formulations for dry powder inhalers typically require greater chemical stability than liquid formulations, but manufacturing powders with the appropriate characteristics for easy aerosolization and alveolar delivery is more complicated.

According to a specific example, the pharmaceutical formulations containing leoligin or leoligin salts as described herein are used in an inhaler as described, for example, in US2004/0019073A1 and as further described herein.

Exemplary atomizers, also referred to as inhalers, essentially consist of an upper housing part, a pump housing, a nozzle, a locking clamp, a spring housing, a spring and a storage container, characterized by: a pump housing fixed in the upper housing part and carrying at one end a nozzle body with the nozzle or nozzle arrangement; a hollow piston with valve body; a power take-off flange in which the hollow body is fixed and which is located in the upper housing part; a locking clamping mechanism located in the upper housing part; a spring housing with the spring located therein, which is rotatably mounted on the upper housing part by means of a rotary bearing; and a lower housing part which is fitted onto the spring housing in the axial direction.

The hollow piston with valve body corresponds to a device disclosed in WO 97/12687. It projects partially into the cylinder of the pump housing and is disposed to be axially movable in the cylinder. Reference is made particularly to FIGS. 1 to 4, especially FIG. 3, and the associated parts of the description. At the moment of release of the spring, the hollow piston with valve body exerts, at its high pressure end, a pressure of 5 MPa to 60 MPa (about 50 bar to 600 bar), preferably 10 MPa to 60 MPa (about 100 bar to 600 bar) on the fluid, the measured amount of active substance solution. Volumes of 10 μL to 50 μL are preferred, volumes of 10 μL to 20 μL are more preferable, whilst a volume of 10 μL to 15 μL per actuation is particularly preferred.

The valve body is preferably mounted at the end of the hollow piston which faces the nozzle body.

The nozzle in the nozzle body is preferably microstructured, i.e., produced by micro-engineering. Microstructured nozzle bodies are disclosed, for example, in WO 99/16530.

The nozzle body consists, for example, of two sheets of glass and/or silicon securely fixed together, at least one of which has one or more microstructured channels which connect the nozzle inlet end to the nozzle outlet end. At the nozzle outlet end there is at least one round or non-round opening 2 to 10 microns deep and 5 to 15 μm wide, the depth preferably being 4.5 to 6.5 μm and the length being 7 to 9 μm.

The nozzle openings are preferably arranged at a spacing of 10 to 200 μm, more preferably at a spacing of 10 to 100 μm, still more preferably 30 to 70 μm. A spacing of 50 μm is most preferred. The directions of spraying therefore meet in the region of the nozzle openings.

When using such atomizer, a liquid pharmaceutical preparation of leoligin or its derivatives is preferred. The liquid pharmaceutical preparation hits the nozzle body at an entry pressure of up to 600 bar, preferably 200 bar to 300 bar and is atomized through the nozzle openings into an inhalable aerosol. The preferred particle sizes of the resulting aerosol are up to 20 μm, preferably 0.1 to 5 μm.

If desired, a plurality of replaceable storage containers containing the fluid to be atomized can be inserted in the atomizer one after another and then used. The storage container contains the aqueous aerosol preparation according to the invention.

The atomizing process is initiated by gently pressing the actuating button. The clamping mechanism then opens the way for the power take-off component. The biased spring pushes the piston into the cylinder in the pump housing. The fluid emerges from the nozzle of the atomizer in the form of a spray.

The nebulizer described above is suitable for nebulizing the aerosol preparations according to the invention to form an aerosol suitable for inhalation. Further useful inhalation drug delivery devices are for example described in Ibrahim et al. Evidence and Research, 8:131-139 (2015).

EXAMPLES

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

Example 1—In Vitro Absorption Studies

Pulmonary absorption studies of systemically active drugs are performed to determine the bioavailability of inhaled formulations. The data on the absorption and transport of inhaled formulations across the lung also provides information concerning the metabolism of drugs in the lung.

For the in vitro absorption studies, the cell line HEBEC3-KT or just HBEC cells, is used to mimic the barrier function of the airway epithelium in vivo. HBEC3-KT was developed from human bronchiole epithelial cells by transduction with retroviral vectors containing the cdk-4 and hTERT gene. The cells show markers and functions of different types of lung epithelial cells. Because of the formation of a suitable epithelial barrier, the pulmonary absorption of drug candidates can be observed. The cells are seeded on trans-well inserts also in an air/liquid interface which mimics the situation in the alveolar region.

Further, the HBEC3-KT cells are used in a co-culture model with fibroblasts on the lower side of the trans-well insert which mimics the airway-blood barrier.

The HBEC cells are treated with 5-methoxyleoligin (5-ML) at concentrations ranging from 1 to 50 μM and the absorption of 5-ML into the cells is assessed.

Data provided include values on absolute concentrations of 5 ML in cells in response to dose and time courses. Further, the ratio of applied 5 ML versus 5 ML taken up by cells is depicted.

Example 2—Permeability Assay

To determine the monolayer permeability of the HBEC3-KT cells, a horseradish peroxidase assay is performed.

To do so, Horseradish peroxidase is added to the media in the upper compartment of the trans-well insert. After different timepoints aliquots of the lower compartment are mixed with TMB/E solution which already has hydrogen peroxide inside to start the reaction. Then the reaction is stopped by $H_2SO_4$ or HCl and read by a spectrometer at a wavelength of 450 nm.

Example 3—Metabolic Stability Assay

To determine the depletion/stability of 5-Methoxyleoligin (5-ML), a metabolic stability assay is performed. 5-ML is used at concentrations ranging from 1 μM to 50 μM. A 100 mM stock solution of 5-ML is diluted 1:10 in DMSO, followed by further dilution in aqueous solution to reach the desired final concentration.

Depletion/Stability of 5-ML is determined by the enzymatic degradation through S9 lung and liver fraction which are made by homogenization and centrifugation of lung cells and liver cells, respectively, at 9000 g.

The S9 subcellular fraction contains enzymes of the cytochrome P450 families as well as Uridine 5'-disphophoglucuronosyltransferase. The S9 cytosolic fraction enzymes are aldehyde oxidase, xanthine oxidase, sulfotransferase, methyltransferase, N-acetyl transferase, and glutathione transferase. The outcome of this assay displays the decomposition rate when 5-ML is delivered through gastric absorption and transformation through liver compared to that when absorbed through lung.

It is important to use a suitable reference substance with known stability under the assay conditions, to check for metabolic competency of the test system. This is done by using Diclofenac, ATRA (all-trans retinoic acid) and/or Retinol, since leoligin and derivatives thereof were found to potently inhibit ATRA signaling. Data provided include percent remaining compound vs. time diagram, disappearance half-live and/or intrinsic clearance.

Further, the depleted 5-ML solution is tested on cell culture to determine toxicity effects of metabolites, if any.

Example 4—Assessment of the Oral Administration Route

To gain insights into the enzymatic stability of a drug, the metabolic stability assay serves as an effective tool and also helps to separate applicable routes for drug uptake from less applicable ones e.g. due to fast hepatic clearance. When substances are applied orally, the liver clearance (first-pass effect) has the most influence on drug clearance and further on the amount of active drug reaching the site of action. Thus, in order to test hepatic clearance, 5-ML was exposed to subcellular fractions of liver and compound concentrations were assessed in a time-dependent manner.

According to Richardson et al., the true rate for stability versus plasma clearance is 43% for S9 (hepatic subcellular fraction) and 45% for hepatocyte cell culture (Richardson et al., *Efficiency in Drug Discovery: Liver S9 Fraction Assay As a Screen for Metabolic Stability*, Drug Metab Lett. 2016; 10(2):83-90).

The concept of in vitro metabolic stability testing is based on and predicts well liver metabolic clearance in vivo. Therefore, the subcellular fraction which accounts for most of the enzymatic activity of the organ is used, which contains intra and extra cellular enzymes of the liver. The elimination half live of 5-ML was calculated by the assessment of the elimination constant.

Results

Figure 3:
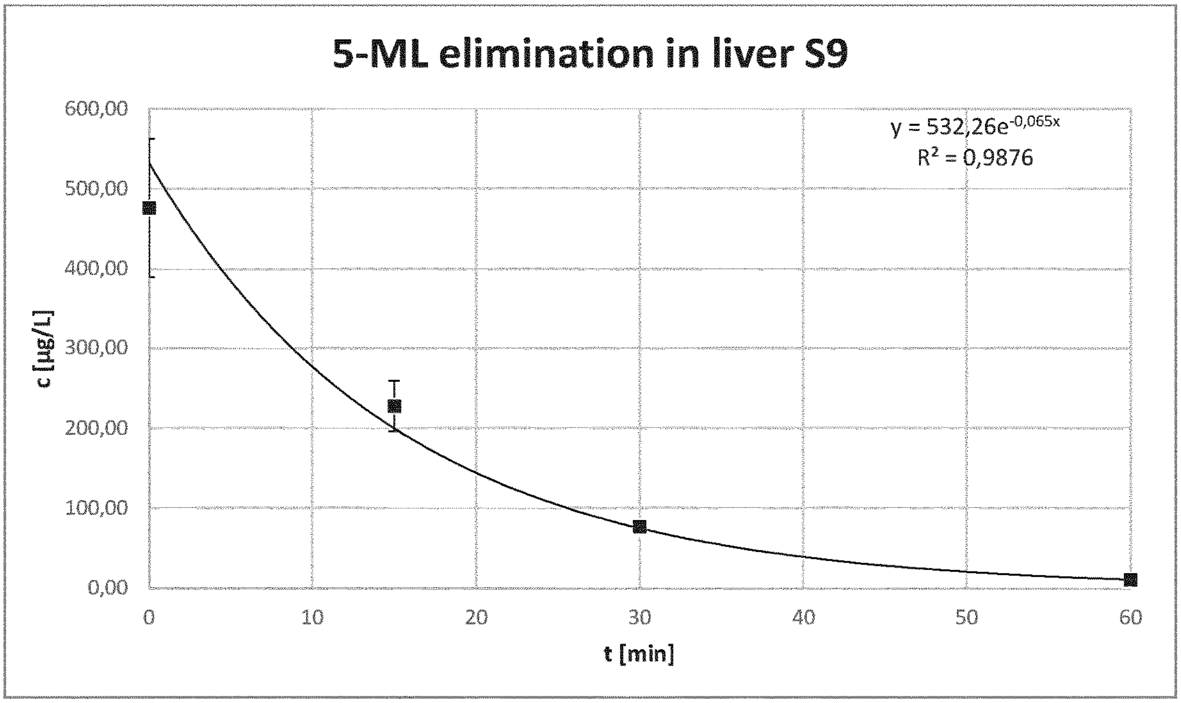
FIG. 3 5-ML is eliminated by liver S9 Extracts over time.

In FIG. 3 the effects of liver S9 extract on 5-ML concentrations over time are depicted. Dots represent median values of three independent experiments. Error bars indicate standard deviations. On the y-axis 5-ML concentration are indicated in μg/L. The x-axis shows the time in minutes and gives the timepoints of measurement 5-ML concentrations. $R^2$ of the first order kinetic exponential function (black line) gave a value of 0,9876. From the elimination constant k the elimination half live was calculated.

The elimination half live of 5-ML in liver S9 was calculated to be 10.66 min, which means that in 10.66 minutes half of a drug is eliminated due to the enzymatic activity of the organ (The elimination half live is calculated by the natural logarithm of 2 (0.693 is the logarithm of 2 and represents the exponential rate of elimination) divided by the elimination constant of an exponential first order kinetic. Which is in this case Ln(2)/0,065 for 5-ML elimination.

To be sure that the assay is working, diclofenac (DCL) was used as reference substance, as valid data for clearance of diclofenac is available. The substance is well described in literature, and it also worked with the HPLC method used for the present Examples. The estimated half live for diclofenac in human liver in literature is 1-3 hours and the assay used herein showed a liver elimination half live for diclofenac of 173 min (2.9 h), confirming robustness and accuracy of the assay.

Materials & Methods for Examples 4 to 6

Materials:

- Human S9 Fraction (H0620.S9 Xenotech)
- Pooled human lung microsomes (H0610.P(NS) Xenotech)
- Pooled Human Saliva non-smoker (IRHUSL5 ML Inovative research)
- Dulbecco's phosphate buffered saline (DPBS) with Mg and Ca (D8662 100 ml Sigma)
- NADPH Tetrasodium salt (481973 Sigma)
- UDPGA Trisodium salt (U6751 Sigma)
- 5-ML
- Diclofenac sodium salt
- Dimethylsulfoxid (DMSO)
- Milli Q Water
- Sodiumhydrogenphosphat (NAOH) 0.1 M
- Acetonitril
- Methanol
- Formic acid
- Shaking inkubator
- Centrifuge
- HPLC Methods:

For the organ specific enzymatic degradation of a compound a reaction mix (1 ml) was made, and aliquots (50 µl) were taken at the timepoints indicated in the Figures to calculate the elimination constant by measuring the compound concentration over time using HPLC-based quantification.

The reaction mix contains:

- Subcellular fraction of the specific organ (Liver S9, Lung microsomes, or Saliva),
- Co-Factor Solution (NADPH and UDPGA). Co-factors are used in this assay to activate the enzymatic activity of the main metabolizing enzymes of the organ specific subcellular fractions. NADPH is needed for the Phase I oxidation where Cytochrome P450 Monoamino-oxidase accounts for the most and UDPGA is needed for the Phase II glucuronidation,
- and the desired compound: 5-ML as active ingredient, Diclofenac as control, water as control; diluted in DMSO.

All compounds were tested in triplicates, except the solvent control (water instead of active compound 5-ML).

Preparation of the reaction mix (in Triplicates):

- Take 980 µl organ specific subcellular fraction solution (0.5 mg/ml) of human liver S9 fraction in DPBS with Calcium and Magnesium,
- Add 10 µl of substance stock solution dissolved in DMSO (c 0,003 M) from either 5-ML, Diclofenac or water as solvent control. This results in a concentration of 5-ML of 3 µM in the reaction mix.

- Dissolve NADPH and UDPGA in 0.1 M NAOH then add 10 µl of NADPH (c 0.05 mg/ml) and UDPGA (0,025 mg/ml) (v:v) 1:2 solution in DPBS to the reaction mix (this has to be mixed together fresh before use) to start the enzymatic activity of the reaction mix,
- Take 50 µl aliquots for timepoint 0 and stop reaction with 1:3 of a Acetonitril:Methanol (v:v) 1:2 solution,
- Incubate the reaction mix in a shaking incubator or shaking water bath at 37° C.,
- Take further aliquots at 15, 30, 60, 120, 240 and 1440 min,
- Centrifuge at 4000 rpm, 10 min at 4° C. and take supernatant for HPLC analysis, and
- Conduct HPLC analysis according to the protocol of JKU Linz Institute of Analytical Chemistry, published by Guntner et al. (Guntner et al. *HPLC- MS/MS Shows That the Cellular Uptake of All- Trans-Retinoic Acid under Hypoxia Is Downregulated by the Novel Active Agent 5-Methoxyleoligin*. Cells 2020, 9, 2048).

Example 5—Assessment of Drug Delivery of 5-ML by Inhalation

As the oral uptake of pure, non-formulated or encapsulated, or chemically stabilized 5 ML does not seem very suitable to target the heart with sufficient amounts of active 5-ML due to the short elimination half-life (liver clearance/first pass effect) other application routes were tested. Therefore, 5-ML was exposed to lung microsomes (drug delivery by inhalation), see Example 5.

Next, 5-ML was exposed to lung microsomes (drug delivery by inhalation).

Materials & Methods

Materials & Methods are the same as in Example 4, except that lung microsomes were used instead of S9 liver fraction.

Results

Figure 4:
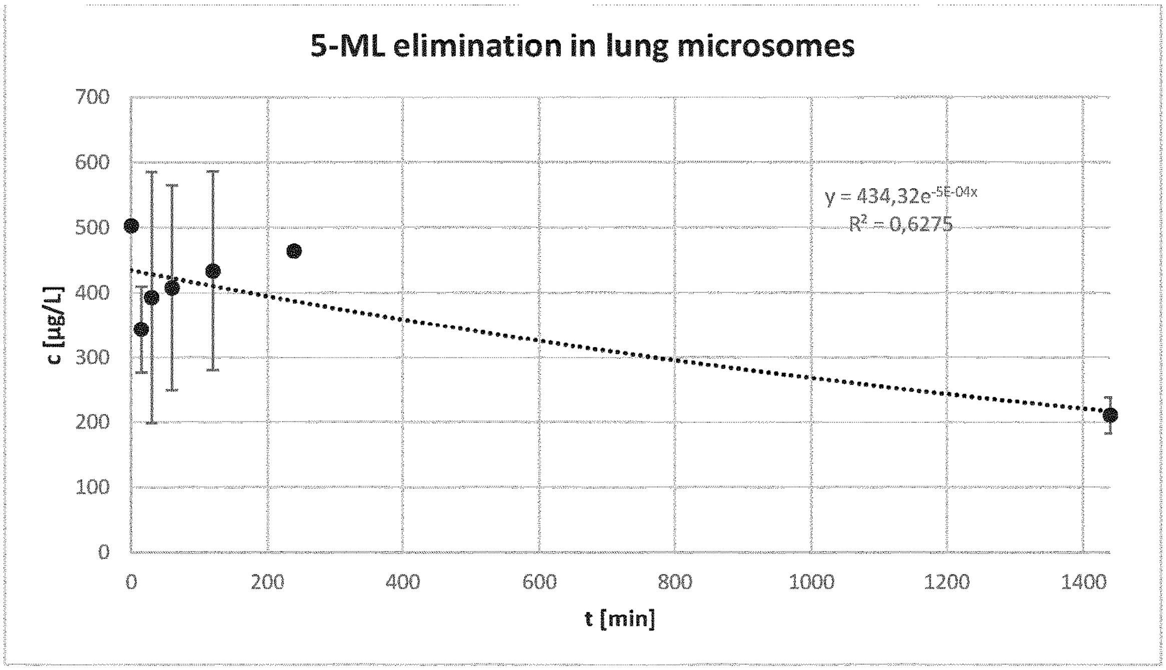

FIG. 4 shows the changes in 5-ML concentration by lung microsomes over time. Dots represent median values of three independent experiments. Error bars indicate standard deviations. On the y-axis 5-ML concentration are given in µg/L. The x-axis shows the time in minutes and gives the timepoints of measurement of 5-ML concentrations. R2of the first order kinetic exponential function (black line) gave a value of 0,6274. From the elimination constant k the elimination half live was calculated.

The data showed that 5-ML has an elimination half live in lung microsomes of 1386 minutes (23.1 h) (FIG. 4). Which is significantly better than the elimination half live in the liver. Thus, drug delivery by inhalation presents a significantly better administration route than oral administration.

Example 6—Assessment of the Buccal Administration Route

As the next step, another non-invasive administration route was tested, namely application of 5 ML through buccal administration.

Materials & Methods

Materials & Methods are the same as in Example 4, except that pooled human saliva was used instead of S9 liver fraction.

In this example, 5-ML was exposed to Saliva—in "setting one" with co-factors (NADPH and UDPGH) and in "setting two" without co-factors.

Subcellular fractions of the buccal mucosa were not tested as they were not (commercially) available.

Results

Figure 5:
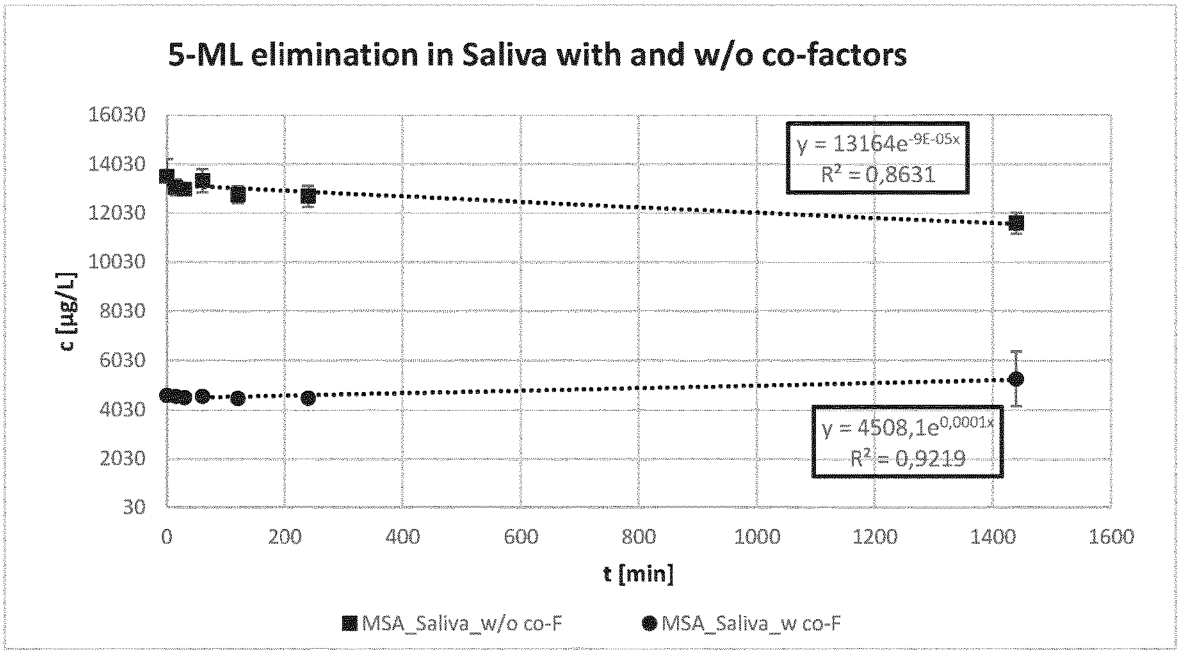

FIG. 5 shows the changes in 5-ML concentration by pooled human saliva over time. The metabolic stability of 5-ML was determined by 1) adding co-factor solution to the assay and 2) in the absence of co-factor solution in the saliva. Dots indicate median values of three independent experiments. Error bars show standard deviations. The y-axis gives 5-ML concentration in μg/L. The x-axis shows the time in minutes and indicates timepoints when the concentration of 5-ML was measured. $R^2$ of the first order kinetic exponential function (black dotted lines) gives a value of 0,8631 for saliva with co-factors, and for samples without co-factor solution $R^2$ was 0,9219. Using the elimination constant k the elimination half live was calculated.

The data for Saliva without co-factor gave an elimination half-life of 115.5 hours (FIG. 5), which includes the submucosal or buccal administration to successful non-invasive administration routes for 5-ML due to very low interference of silva with the drug.

The data for Saliva with co-factors surprisingly showed no elimination, and even a slight increase in 5-ML concentration over time (FIG. 5). This further emphasizes that submucosal or buccal administration is a highly efficient route of administration for 5-ML.

These data show that the buccal administration routes are highly effective for 5-ML.

The invention claimed is:

1. A method for reduction of tissue damage caused by vascular obliteration or associated with hypoxia, comprising the step of systemically administering an effective amount of a compound selected from one of the following compounds to a subject in need thereof:

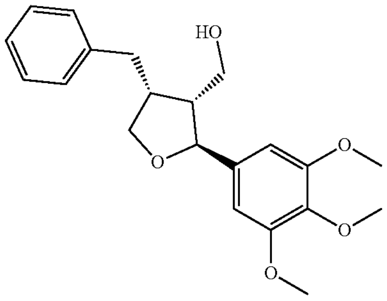 [SMILES: COc1cc([C@H]2OC[C@H](Cc3ccccc3)[C@@H]2CO)cc(OC)c1OC]

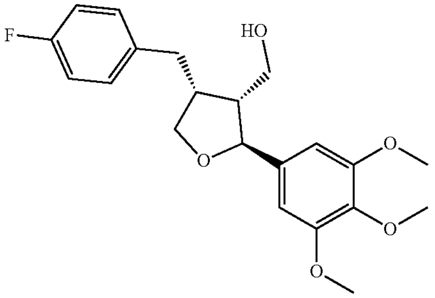 [SMILES: COc1cc([C@H]2OC[C@H](Cc3ccc(F)cc3)[C@@H]2CO)cc(OC)c1OC]

-continued

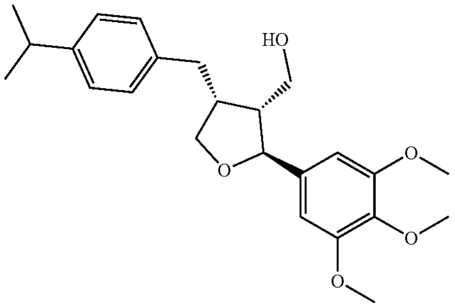 [SMILES: COc1cc([C@H]2OC[C@H](Cc3ccc(C(C)C)cc3)[C@@H]2CO)cc(OC)c1OC]

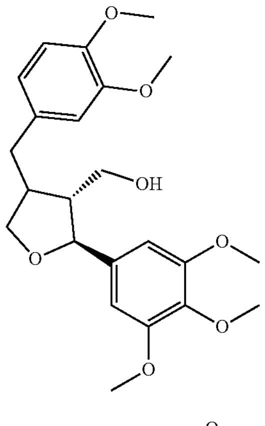

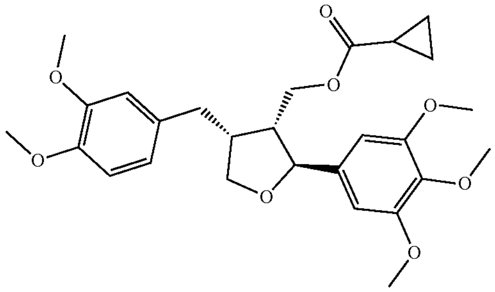

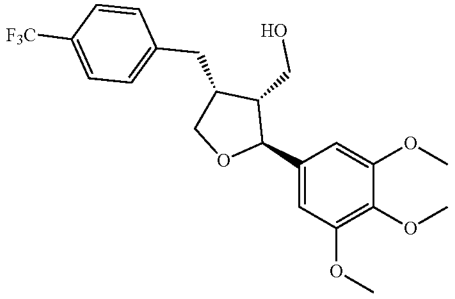 [SMILES: COc1cc([C@H]2OC[C@H](Cc3ccc(C(F)(F)F)cc3)[C@@H]2CO)cc(OC)c1OC]

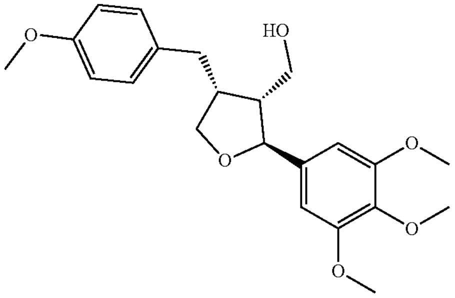

-continued

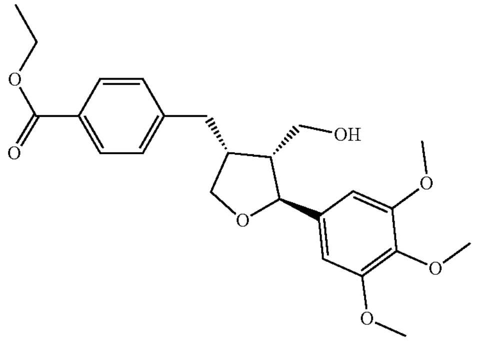 [SMILES: CCOC(=O)c1ccc(C[C@H]2CO[C@H](c3cc(OC)c(OC)c(OC)c3)[C@H]2CO)cc1]

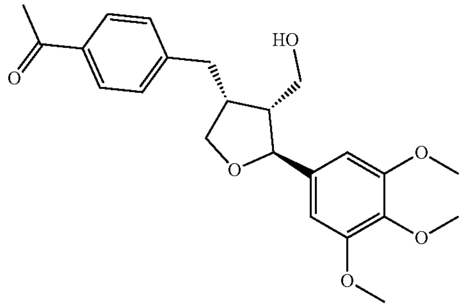 [SMILES: COc1cc([C@H]2OC[C@H](Cc3ccc(C(C)=O)cc3)[C@@H]2CO)cc(OC)c1OC]

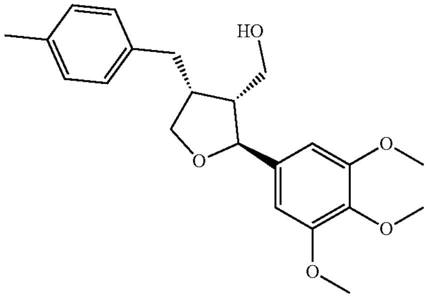

-continued

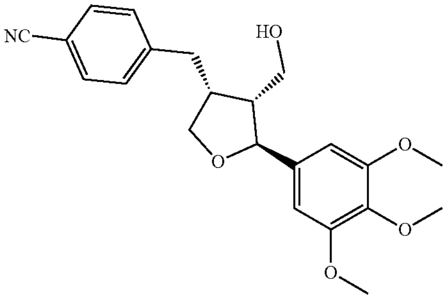 [SMILES: COc1cc([C@H]2OC[C@H](Cc3ccc(C#N)cc3)[C@@H]2CO)cc(OC)c1OC]

wherein the compound is administered in an amount of about 0.15 to 15 mg/kg body weight of the subject via the respiratory tract, buccal administration, or sublingual administration.

2. The method of claim 1, wherein the tissue damage is to a tissue selected from the group consisting of heart, brain, kidney, bowel, liver, skeletal muscle, and skin.

3. The method of claim 1, wherein the compound is administered by inhalation.

4. The method of claim 1, wherein the compound is administered by an inhaler.

5. The method of claim 1, wherein the compound is administered via buccal and/or sublingual administration.

6. The method of claim 1, wherein the compound is administered by non-invasive self-administration.

7. The method of claim 1, wherein the compound is administered when in acute need or at least once daily.

8. The method of claim 1, wherein the compound is provided as a liquid or solid formulation.

9. The method of claim 1, wherein the subject in need thereof is a human subject.

* * * * *